(12) United States Patent
Sieck et al.

(10) Patent No.: US 10,118,754 B2
(45) Date of Patent: Nov. 6, 2018

(54) METHOD OF FOLDING PANT-LIKE DISPOSABLE ABSORBENT GARMENTS IN A CHUTE

(75) Inventors: Jason K. Sieck, Neenah, WI (US); Bradley Schoon, Oshkosh, WI (US); Brian R. Vogt, Winneconne, WI (US); Stephen A. Kolasinski, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1535 days.

(21) Appl. No.: 13/302,508

(22) Filed: Nov. 22, 2011

(65) Prior Publication Data
US 2013/0130880 A1   May 23, 2013

(51) Int. Cl.
| | |
|---|---|
| *B31B 1/26* | (2006.01) |
| *B31F 1/00* | (2006.01) |
| *B31F 1/30* | (2006.01) |
| *B65D 85/18* | (2006.01) |
| *A61F 13/15* | (2006.01) |
| *B65H 45/04* | (2006.01) |

(52) U.S. Cl.
CPC ........ *B65D 85/18* (2013.01); *A61F 13/15747* (2013.01); *B65H 45/04* (2013.01)

(58) Field of Classification Search
CPC ............... B65D 85/18; A61F 13/15747; A61F 13/5633; A61F 13/15699; A61F 13/49061; A61F 13/565; B65H 2801/57
USPC .......... 53/429; 493/405, 423, 440, 441, 421, 493/455–457
See application file for complete search history.

(56) References Cited

U.S. PATENT DOCUMENTS

| | | | |
|---|---|---|---|
| 3,572,689 A | | 3/1971 | Murphy |
| 3,635,462 A | * | 1/1972 | Joa ................................ 493/394 |

(Continued)

FOREIGN PATENT DOCUMENTS

| | | |
|---|---|---|
| CN | 1770989 A | 5/2006 |
| EP | 0 119 827 B1 | 7/1988 |

(Continued)

OTHER PUBLICATIONS

Co-pending U.S. Appl. No. 13/302,429, filed Nov. 22, 2011, by Schoon et al. for "Method of Folding Pant-Like Disposable Absorbent Garments in a Trough."

*Primary Examiner* — Andrew M Tecco
*Assistant Examiner* — Eyamindae Jallow
(74) *Attorney, Agent, or Firm* — Kimberly-Clark Worldwide, Inc.

(57) ABSTRACT

A method of folding a pant-like disposable absorbent garment includes providing a garment defining first and second waist side regions, a waist center region positioned therebetween, and a crotch region longitudinally below the waist center region. In particular embodiments, the method further includes folding the garment along a transversely extending fold line so as to bring the crotch region into superposed relation with the waist center region; providing a chute having a floor and first and second side walls; urging the garment into the chute; and, while the garment is in the chute, folding the garment along longitudinally extending first and second fold lines so as to position the first and second waist side regions over the waist center region. The first and second fold lines are adjacent the first and second side walls, respectively.

4 Claims, 25 Drawing Sheets

(56) References Cited

U.S. PATENT DOCUMENTS

| | | | |
|---|---|---|---|
| 4,326,528 A | 4/1982 | Ryan | |
| 4,614,512 A * | 9/1986 | Capdeboscq | 493/441 |
| 4,701,156 A | 10/1987 | Larsonneur | |
| 5,046,272 A * | 9/1991 | Vogt et al. | 38/143 |
| 5,176,615 A * | 1/1993 | Munsch | 493/427 |
| 5,300,007 A * | 4/1994 | Kober | 493/23 |
| 5,601,547 A * | 2/1997 | Kato et al. | 604/385.3 |
| 5,776,121 A * | 7/1998 | Roe et al. | 604/385.25 |
| 5,868,727 A | 2/1999 | Barr et al. | |
| 5,997,459 A | 12/1999 | Krueger et al. | |
| 6,015,934 A * | 1/2000 | Lee et al. | 604/358 |
| 6,305,146 B1 | 10/2001 | Gerber | 53/116 |
| 6,514,187 B2 * | 2/2003 | Coenen et al. | 493/418 |
| 6,601,705 B2 | 8/2003 | Molina | |
| 6,669,618 B2 * | 12/2003 | Reising et al. | 493/394 |
| 6,699,166 B2 * | 3/2004 | Walter et al. | 493/446 |
| 6,723,035 B2 | 4/2004 | Franklin et al. | |
| 6,846,374 B2 * | 1/2005 | Popp et al. | 156/85 |
| 6,923,926 B2 * | 8/2005 | Walter et al. | 264/119 |
| 7,021,466 B2 | 4/2006 | Kuske | |
| 7,150,137 B2 | 12/2006 | Tippey | |
| 7,399,266 B2 | 7/2008 | Aiolfi | |
| 7,617,656 B2 * | 11/2009 | Wiedmann | 53/429 |
| 8,105,304 B2 | 1/2012 | Uda | |
| 8,439,814 B2 * | 5/2013 | Piantoni et al. | 493/416 |
| 8,440,039 B2 * | 5/2013 | Nakakado | 156/204 |
| 8,496,778 B2 * | 7/2013 | Vasic | 156/253 |
| 8,663,411 B2 * | 3/2014 | McCabe | 156/66 |
| 8,672,824 B2 * | 3/2014 | Sablone et al. | 493/441 |
| 2003/0062113 A1 * | 4/2003 | Van Eperen et al. | 156/227 |
| 2003/0062121 A1 * | 4/2003 | Franklin et al. | 156/285 |
| 2003/0226862 A1 * | 12/2003 | Vogt et al. | 223/37 |
| 2004/0048727 A1 | 3/2004 | Roozrokh | |
| 2004/0054342 A1 * | 3/2004 | Newbill et al. | 604/368 |
| 2004/0110618 A1 | 6/2004 | Kubalek et al. | |
| 2004/0185996 A1 * | 9/2004 | Franklin et al. | 493/405 |
| 2007/0107918 A1 | 5/2007 | Coe et al. | |
| 2007/0142194 A1 | 6/2007 | Coenen et al. | |
| 2007/0144937 A1 | 6/2007 | Gilroy | |
| 2007/0267322 A1 | 11/2007 | Kishida | |
| 2008/0134641 A1 | 6/2008 | Corlett | |
| 2008/0276570 A1 * | 11/2008 | Kuroda et al. | 53/412 |
| 2010/0072108 A1 | 3/2010 | Underhill | |
| 2010/0179042 A1 | 7/2010 | Yamamoto | |
| 2011/0167765 A1 * | 7/2011 | Yamamoto | 53/429 |
| 2011/0209269 A1 | 9/2011 | Kinoshita et al. | |
| 2011/0251038 A1 * | 10/2011 | LaVon et al. | 493/405 |
| 2012/0028777 A1 * | 2/2012 | Knecht | 493/393 |
| 2012/0043244 A1 | 2/2012 | Hagner et al. | |
| 2012/0043245 A1 | 2/2012 | Hagner et al. | |
| 2012/0077661 A1 * | 3/2012 | Oonishi et al. | 493/471 |
| 2012/0083399 A1 * | 4/2012 | Putzer et al. | 493/343 |
| 2012/0095429 A1 * | 4/2012 | Kobayashi et al. | 604/385.16 |
| 2012/0152447 A1 * | 6/2012 | Schneider | 156/227 |
| 2012/0172828 A1 * | 7/2012 | Koenig et al. | 604/385.201 |
| 2012/0208688 A1 * | 8/2012 | Sakaguchi et al. | 493/343 |
| 2012/0225764 A1 * | 9/2012 | Ogasawara | 493/405 |
| 2012/0324633 A1 * | 12/2012 | Back et al. | 2/400 |
| 2013/0296152 A1 * | 11/2013 | Murakami et al. | 493/405 |
| 2014/0378287 A1 * | 12/2014 | Schneider et al. | 493/405 |

FOREIGN PATENT DOCUMENTS

| | | |
|---|---|---|
| EP | 0 452 951 B1 | 11/1995 |
| EP | 1 933 796 B1 | 7/2010 |
| EP | 1 954 230 B1 | 1/2011 |
| JP | 58-013704 A | 1/1983 |
| JP | 01-009177 A | 1/1989 |
| JP | 04-266360 A | 9/1992 |
| JP | 09-099903 A | 4/1997 |
| JP | 09-131364 A | 5/1997 |
| JP | 10-095481 A | 4/1998 |
| JP | 11-113956 A | 4/1999 |
| JP | 2994345 B1 | 12/1999 |
| JP | 2000-024029 A | 1/2000 |
| JP | 2000-024030 A | 1/2000 |
| JP | 2001-019070 A | 1/2001 |
| JP | 2003-093436 A | 4/2003 |
| JP | 2003-250826 A | 9/2003 |
| JP | 2004-248785 A | 9/2004 |
| JP | 2006-247429 A | 9/2006 |
| WO | WO 2002/007665 A1 | 1/2002 |
| WO | WO 2004/108043 A1 | 12/2004 |
| WO | WO 2008/155702 A1 | 12/2008 |
| WO | WO 2009/083788 A1 | 7/2009 |
| WO | WO 2010/089964 A1 | 8/2010 |
| WO | WO 2010/101277 A1 | 9/2010 |

* cited by examiner

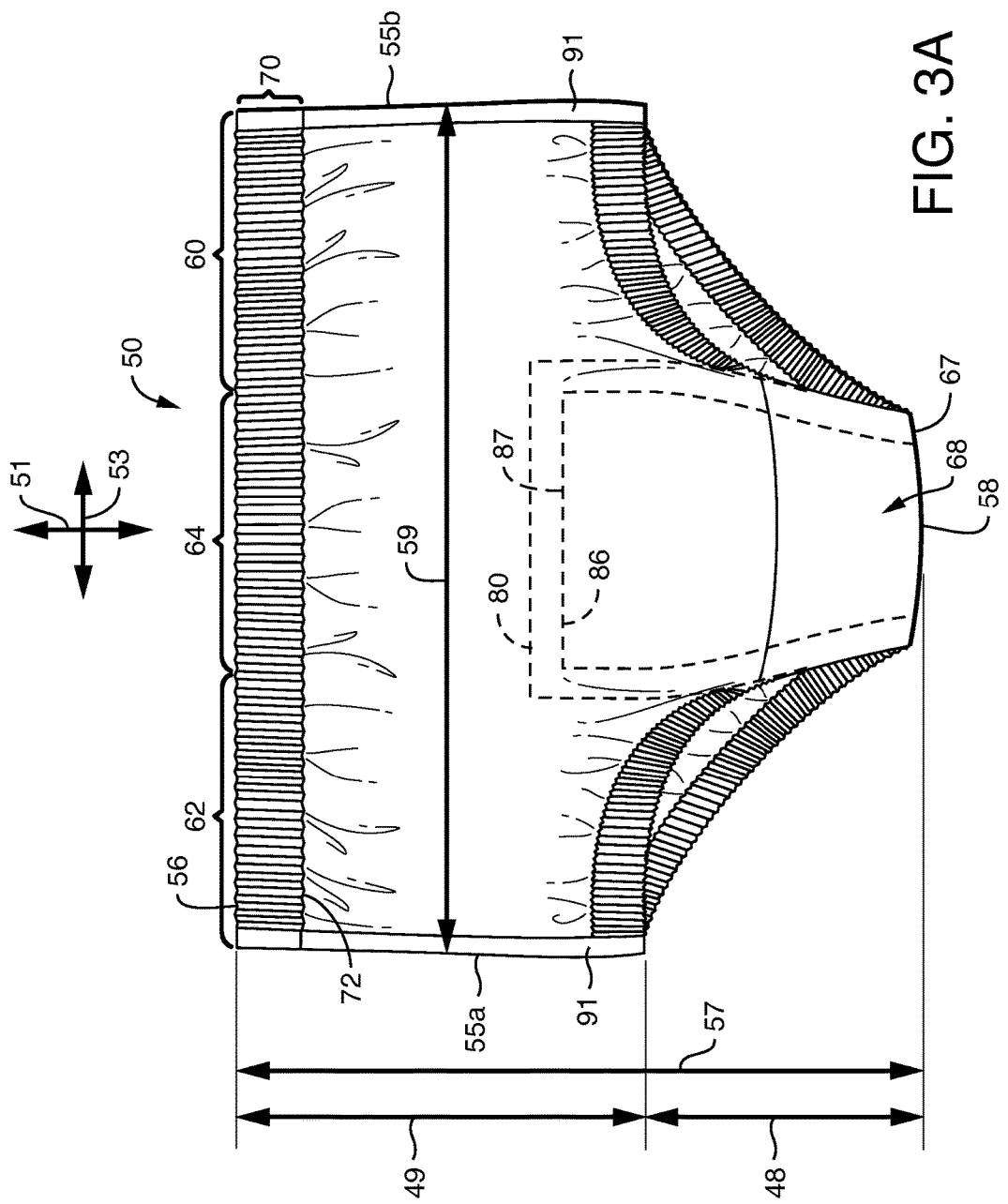

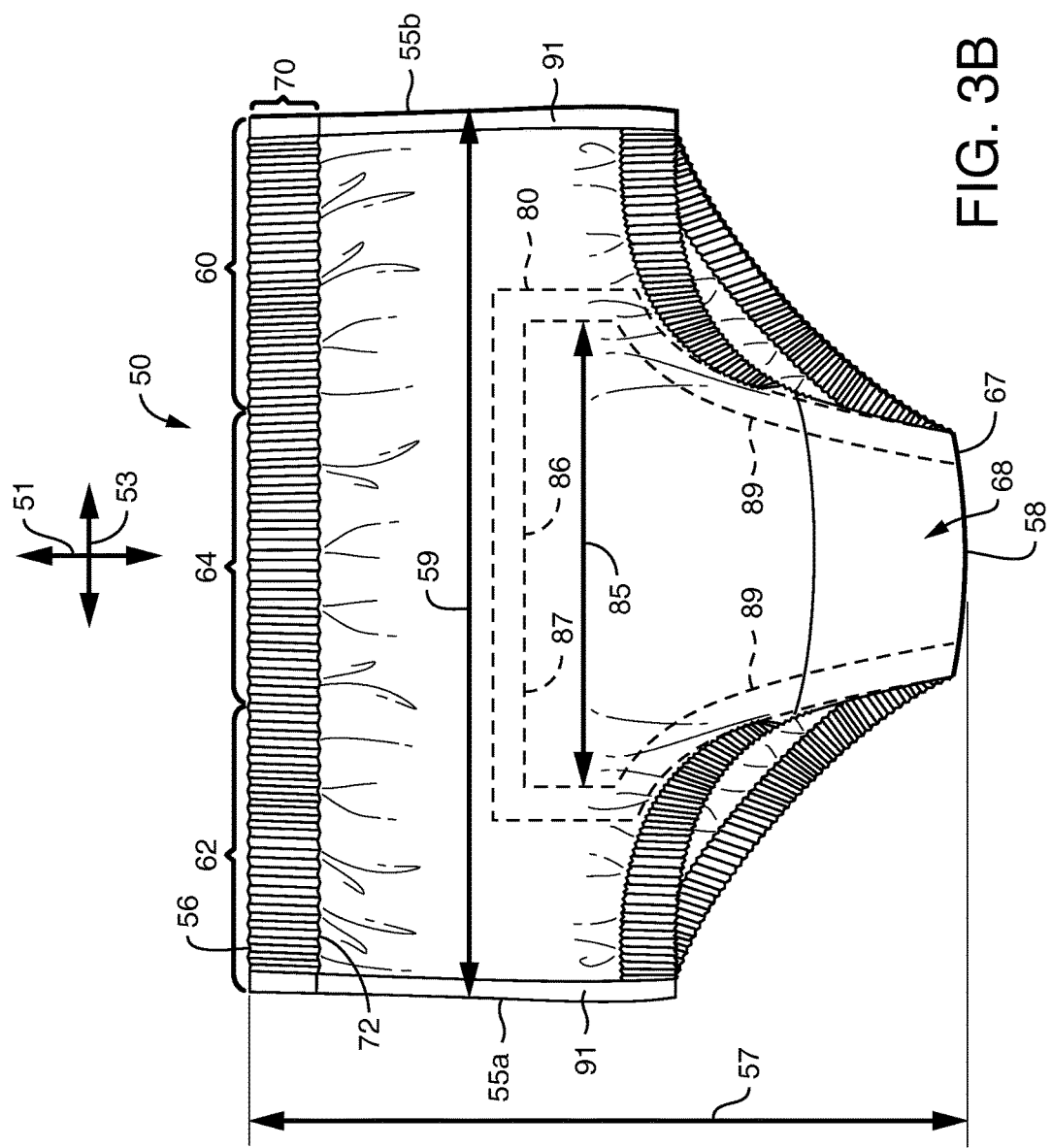

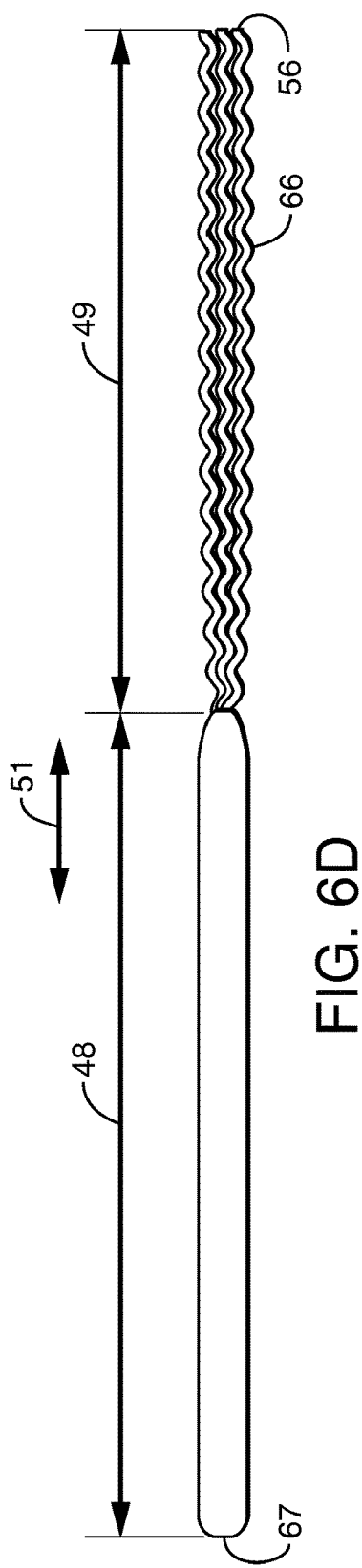
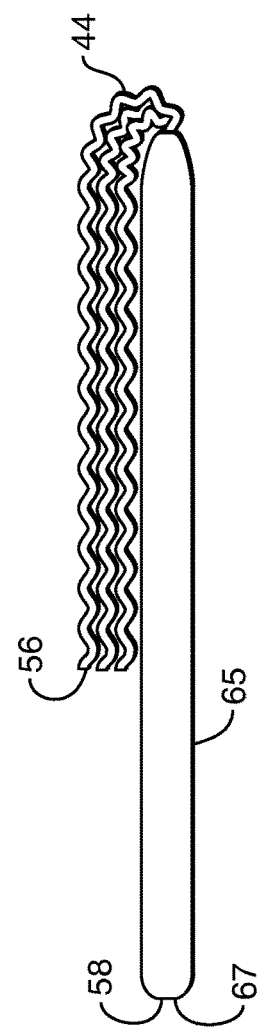

METHOD OF FOLDING PANT-LIKE DISPOSABLE ABSORBENT GARMENTS IN A CHUTE

BACKGROUND

People rely on disposable absorbent garments in their everyday lives, including such garments as adult incontinence products, enuresis pants, training pants, and diapers. Many manufacturers seek to better meet the needs of users of such products. With certain products, such as adult incontinence underwear and enuresis pants, it is important that the garments look and feel as much as possible like "regular" underwear to promote an improved sense of normalcy to the wearer who suffers from incontinence or enuresis. Additionally, purchasers and users of such products are frequently embarrassed about their condition and about having to purchase products to deal with their incontinence or enuresis condition.

Currently, the most common method for obtaining incontinence and enuresis underwear is by purchasing a plurality of such garments packaged in bags. Typically, the garments are folded in some manner to better fit within the package. Consistent folding of the garments is important for a number of reasons. First, disposable absorbent garments are typically manufactured at a high rate of speed; stacks of folded garments are rapidly and repeatedly pushed into packaging materials, such as flexible plastic bags. Inconsistent folding of the garments can result in bulging or lumpy stacks of folded garments, which can interfere with the automated packaging operation. Second, bulging and lumpy stacks of folded garments result in bulging, uneven filled packages, which can cause the packages to be unstable on retail shelves, as well as appear to the consumer to be suffering in quality. Third, upon removing haphazardly, non-neatly folded garments from the package, consumers may be left with a negative impression of quality. Indeed, poor, unpredictable folding can in some cases impact the performance of the absorbent garment, by creating creases or cracks in the fluid-absorbing core at inopportune locations.

Conventional methods of folding pant-like, disposable absorbent garments are suboptimal. Therefore, what is needed is an improved method of folding pant-like, disposable absorbent garments to promote consistent, predictable, and controlled folding of the garments in high-speed manufacturing processes.

SUMMARY OF THE INVENTION

The present invention is directed to a method of folding a pant-like disposable absorbent garment. The method defines a machine direction, a cross-machine direction, and a vertical direction generally perpendicular to both the machine direction and the cross-machine direction. The machine direction and the cross-machine direction together define a transport plan. In particular embodiments, the method comprises providing a garment, the garment having a waist opening and two leg openings. The garment defines a longitudinal direction and a transverse direction. The garment defines a first waist side region adjacent a first side edge, a second waist side region adjacent a second side edge, a waist center region positioned transversely between the first waist side region and the second waist side region, and a crotch region longitudinally adjacent the waist center region. The garment further includes an absorbent core.

The method in further includes providing a chute. The chute comprises a first side wall and a second side wall, and defines chute width extending from the first side wall to the second side wall. The chute defines a first end having a first opening and a second end having a second opening, and the chute extends from the first end to the second end in the vertical direction.

The method further includes transporting the garment in the machine direction, such that the longitudinal and transverse directions of the garment lie substantially within the transport plane; positioning the garment over the first opening of the chute; urging the garment into the chute; transporting the garment in the vertical direction within the chute; and folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the garment is in the chute.

In particular embodiments, the chute width extends in a direction parallel to the cross-machine direction, and the longitudinal direction of each garment is in parallel alignment with the machine direction during the transporting of the garment in the machine direction.

In other embodiments, the chute width extends in a direction parallel to the machine direction, and the longitudinal direction of the each garment is in parallel alignment with the cross-machine direction during the transporting of the garment in the machine direction.

BRIEF DESCRIPTION OF THE DRAWINGS

FIG. 3A representatively illustrates a front plan view of the disposable absorbent pant of FIG. 2, shown in a relaxed and laid-flat condition.

FIG. 3B representatively illustrates a front plan view of an alternative embodiment of disposable absorbent pant, shown in a relaxed and laid-flat condition FIG. 4A representatively illustrates a front plan view of an intermediate folded configuration of the disposable absorbent pant of FIG. 3, shown in a transversely tensioned condition, with one longitudinal fold.

FIG. 6D is a cross-sectional view of the pant of FIG. 6C as viewed along line 6D-6D.

FIG. 6E is similar to the view of FIG. 6D, but includes one longitudinal fold.

DEFINITIONS

Figure 1:
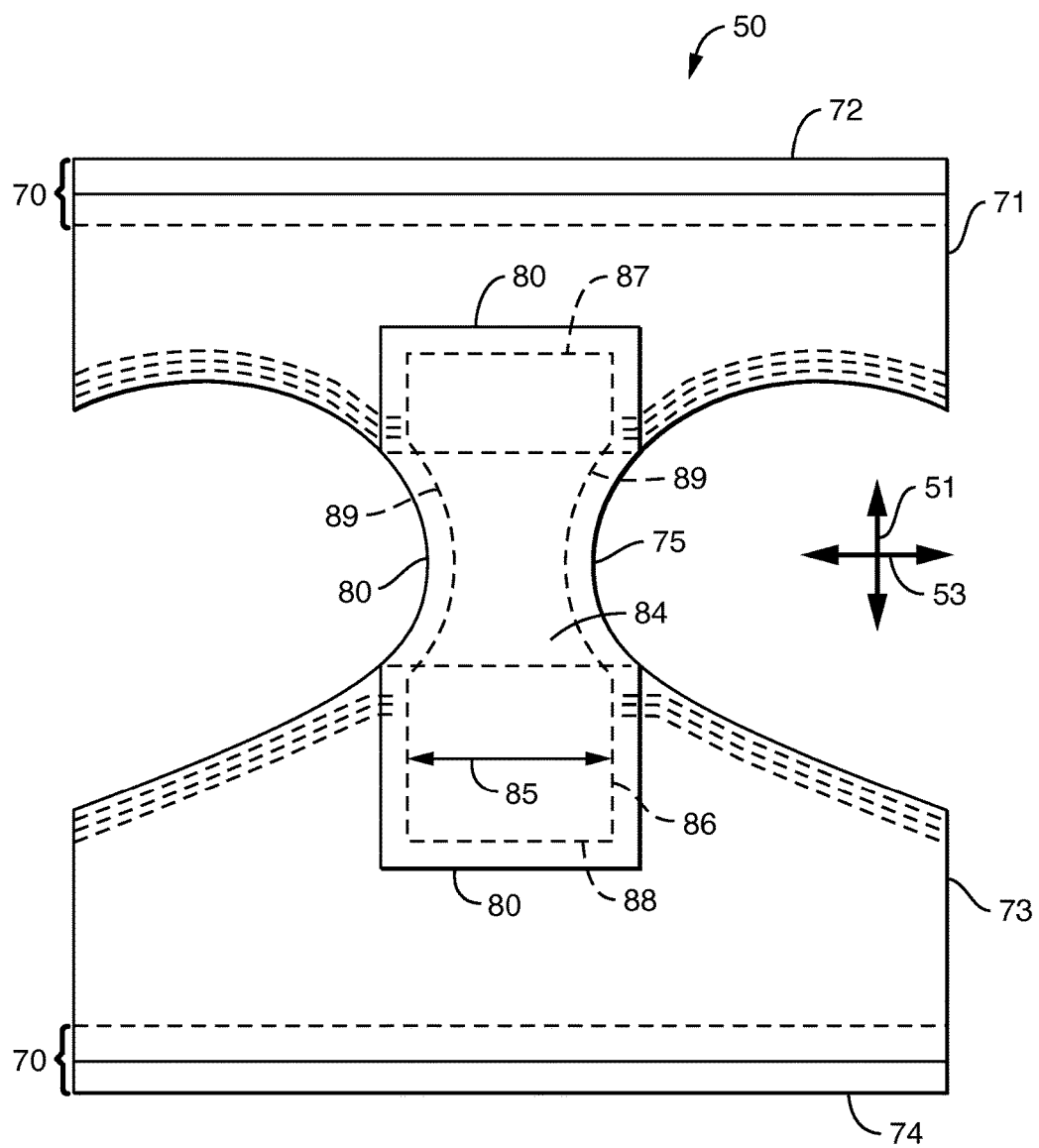
FIG. 1 representatively illustrates a plan view of one embodiment of a disposable absorbent pant suitable for use in conjunction with certain embodiments of the present invention in a longitudinally stretched and laid-flat condition, prior to the joining of the front and back waist regions, and showing the surface of the article that faces the wearer when the article is worn.
Figure 2:
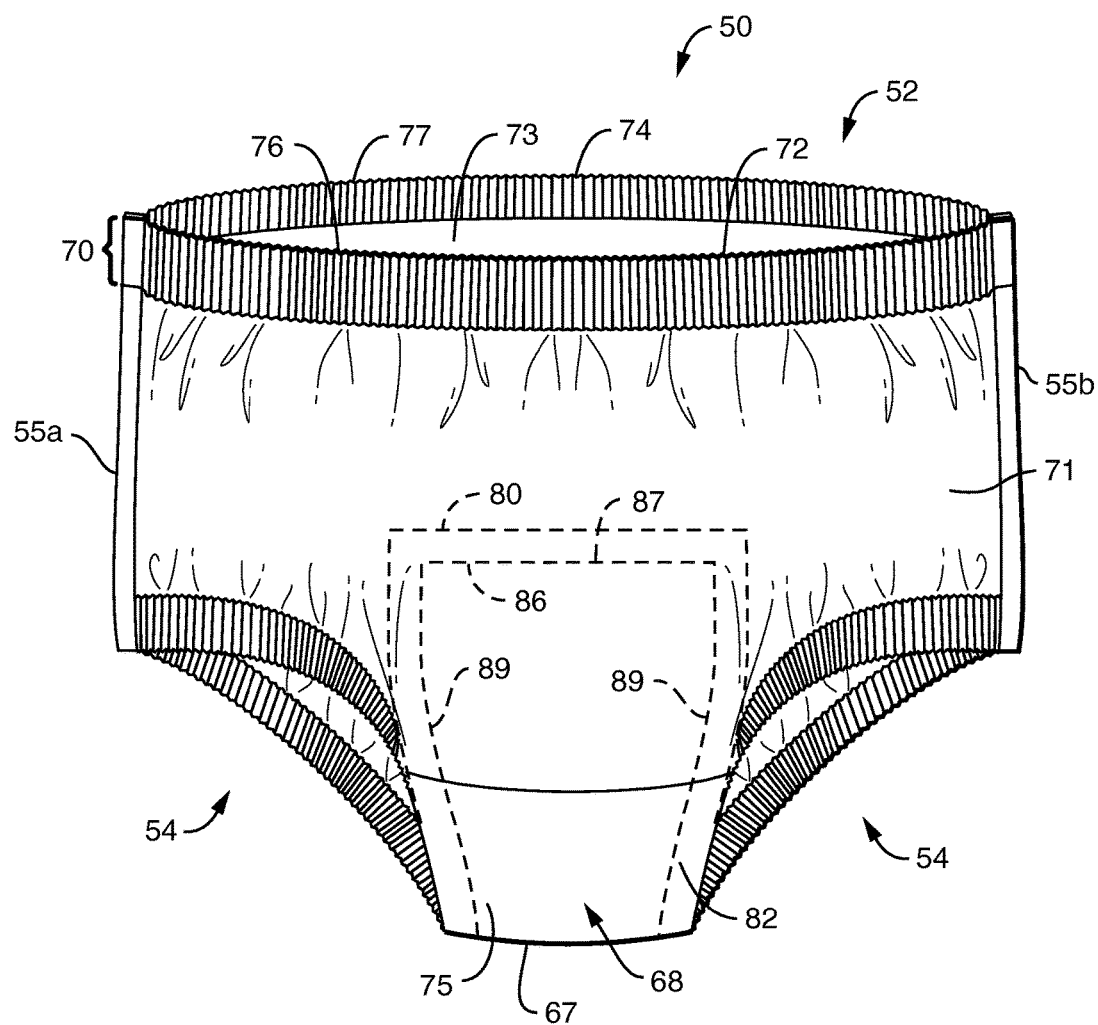
FIG. 2 representatively illustrates a front perspective view of the exemplary embodiment of FIG. 1, shown in a fully assembled condition.
Figure 4A:
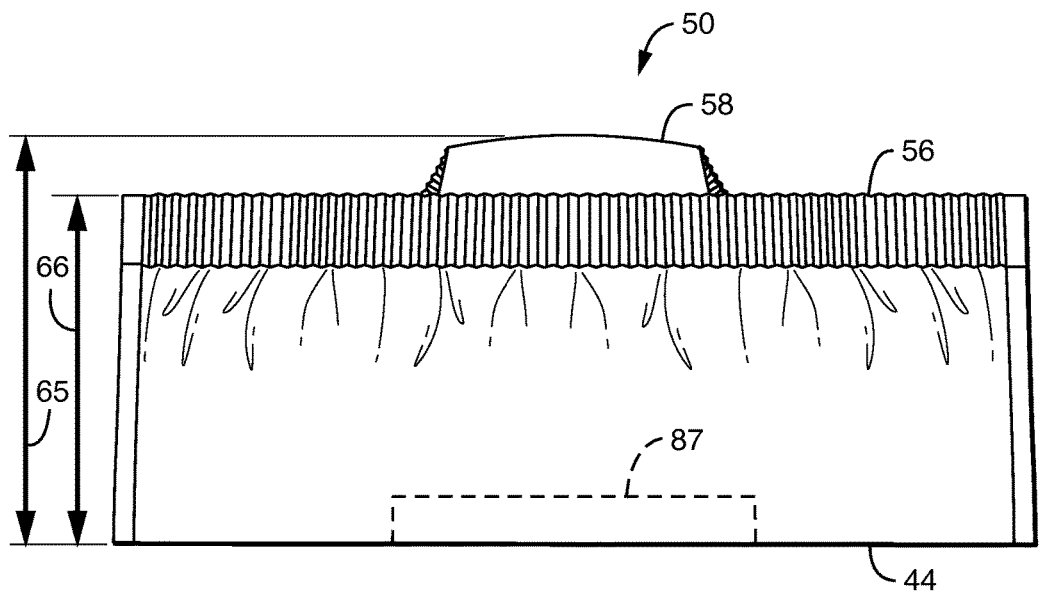
FIG. 4B representatively illustrates a back plan view of an intermediate folded configuration of the disposable absorbent pant of FIG. 3, shown in a transversely tensioned condition, with one longitudinal fold.
FIG. 4C representatively illustrates a front plan view of a fully folded configuration of the disposable absorbent pant of FIG. 3, with both waist side regions folded under the waist center region.
FIG. 4D representatively illustrates a back plan view of a fully folded configuration of the disposable absorbent pant of FIG. 3, with both waist side region folded over the waist center region.
Figure 4B:
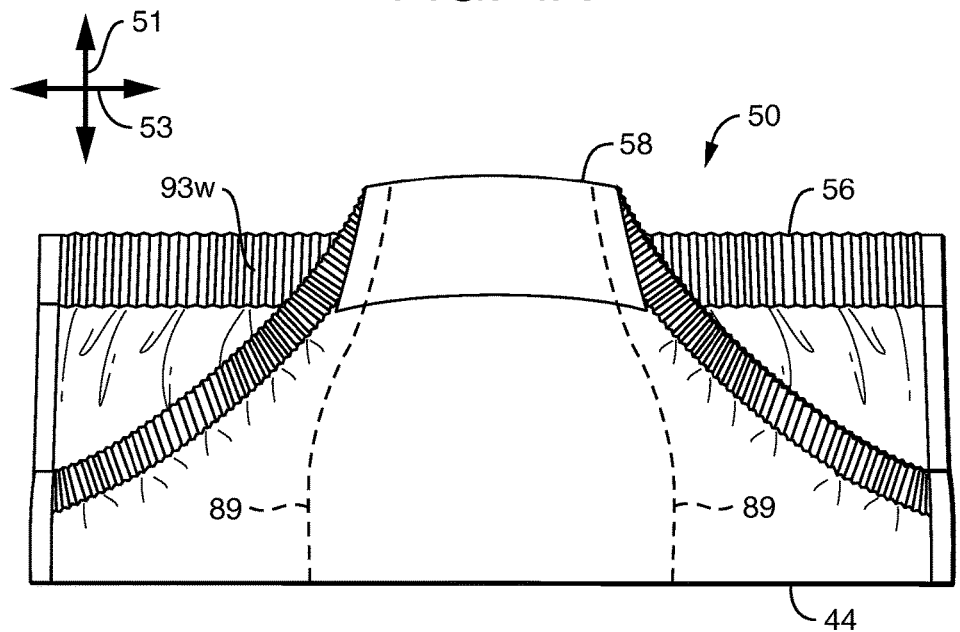
Figure 4C:
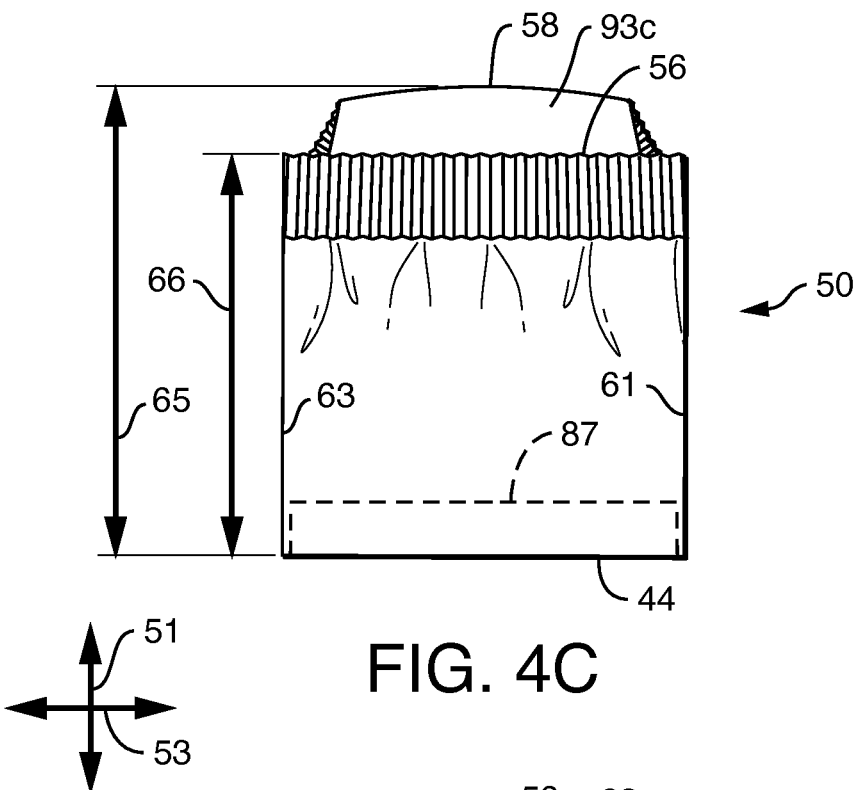
Figure 4D:
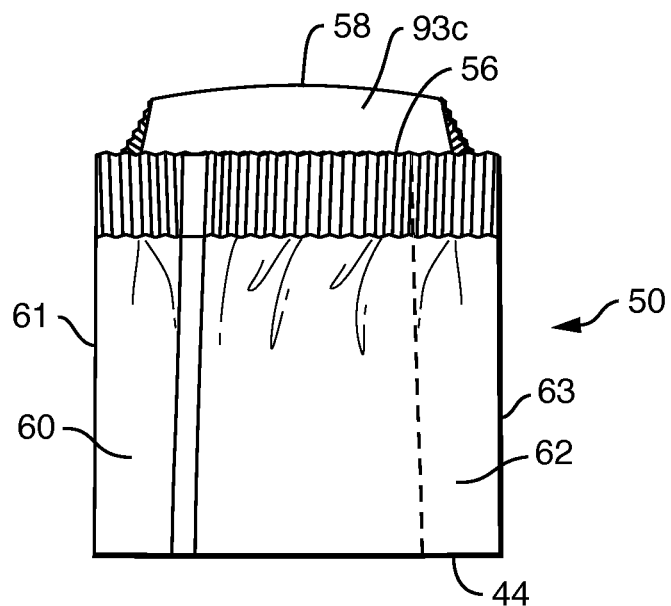
Figure 5A:
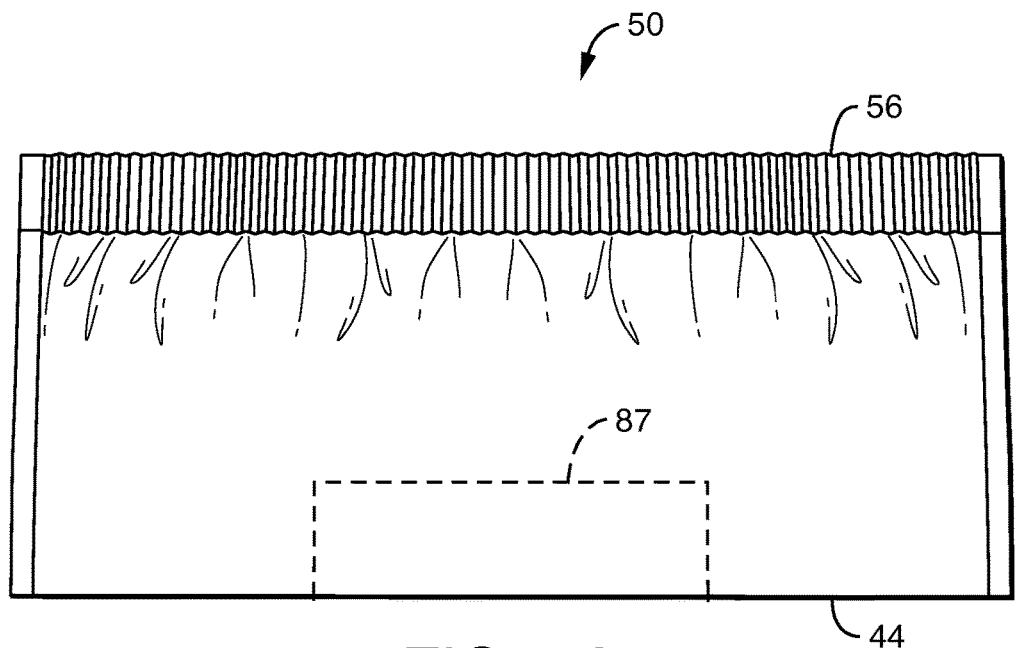
FIG. 5A representatively illustrates a front plan view of an alternative intermediate folded configuration of the disposable absorbent pant of FIG. 3, shown in a transversely tensioned condition, with one longitudinal fold.
Figure 5B:
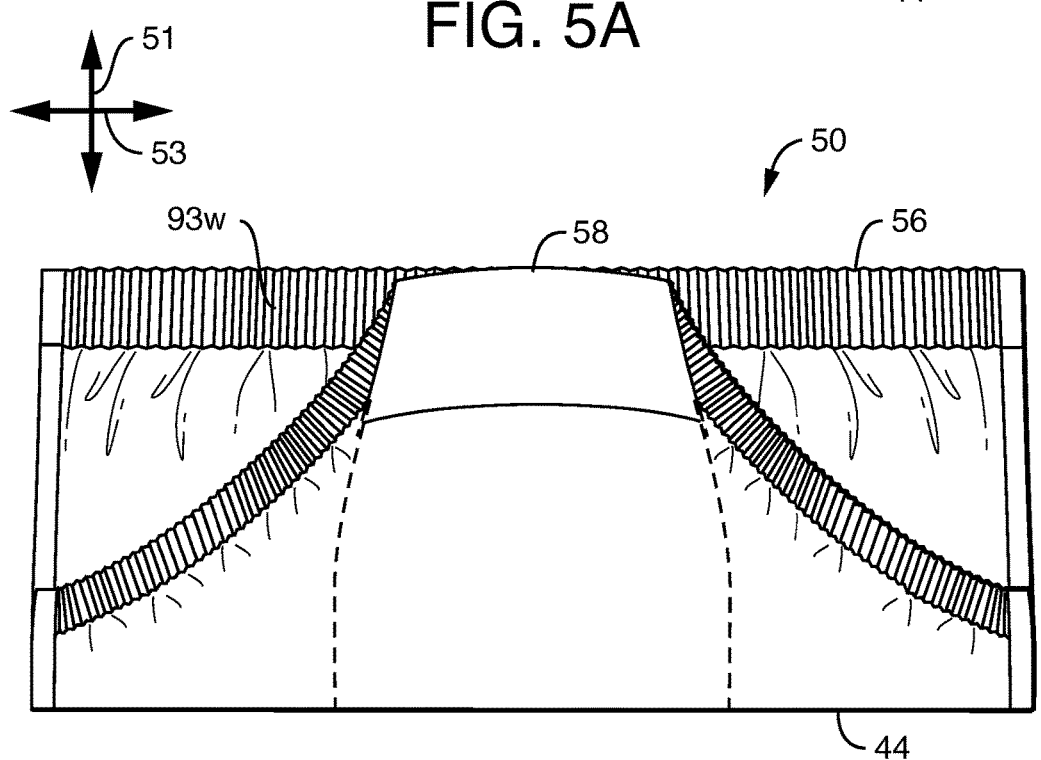
FIG. 5B representatively illustrates a back plan view of an alternative intermediate folded configuration of the disposable absorbent pant of FIG. 3, shown in a transversely tensioned condition, with one longitudinal fold.
Figure 5C:
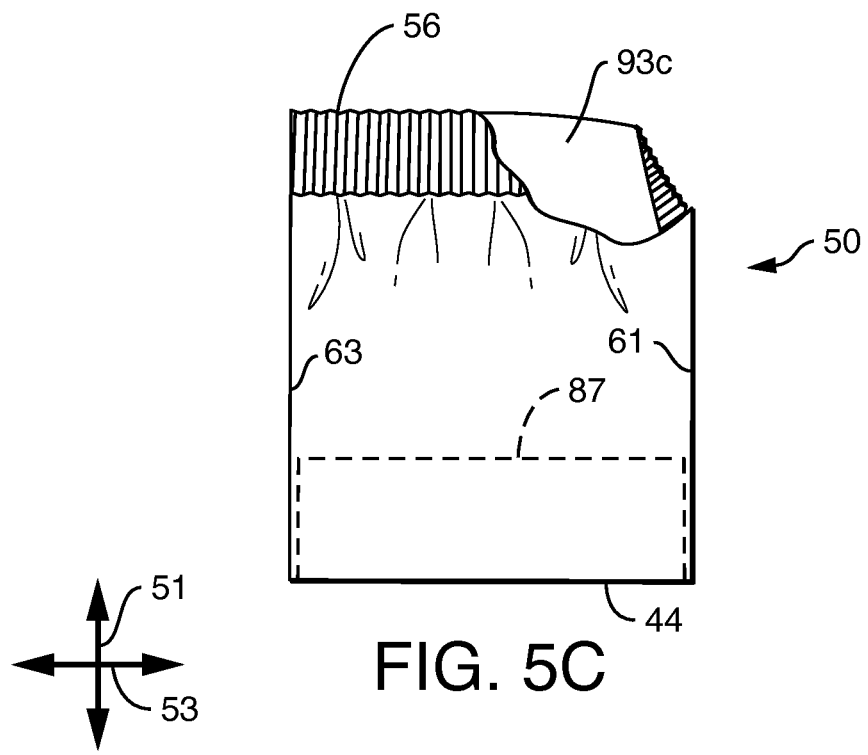
FIG. 5C representatively illustrates a front plan view of an alternative fully folded configuration of the disposable absorbent pant of FIG. 3, with both waist side regions folded under the waist center region, and with portions cut away to show underlying features.
Figure 5D:
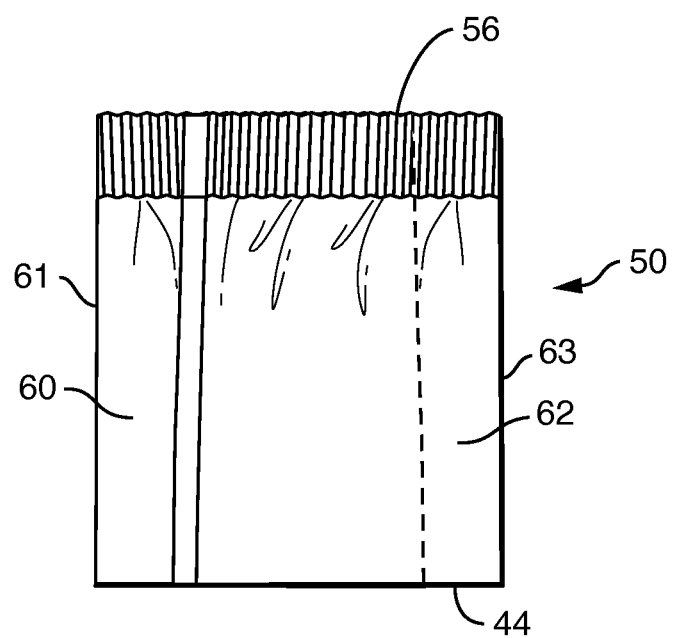
FIG. 5D representatively illustrates a back plan view of an alternative fully folded configuration of the disposable absorbent pant of FIG. 3, with both waist side regions folded over the waist center region.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

"Integral" is used to refer to various portions of a single unitary element rather than separate structures bonded to or placed with or placed near one another.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis.

These terms may be defined with additional language in the remaining portions of the specification.

DETAILED DESCRIPTION OF EXEMPLARY EMBODIMENTS

The present invention relates to a method 20 of folding a pant-like disposable absorbent garment. Reference to the Figures shall be made in describing various embodiments of the invention. It should be noted that the embodiments depicted in the Figures and described herein are merely representative examples of the method of the invention. The various embodiments of the invention are suitable for use in folding disposable absorbent garments such as adult incontinence underwear, prefastened disposable diapers, disposable swim pants, disposable training pants, disposable enuresis garments, and the like. For illustration purposes, various embodiments of the present method invention shall be described in conjunction with the folding of pull-on style incontinence pants.

Figure 6A:
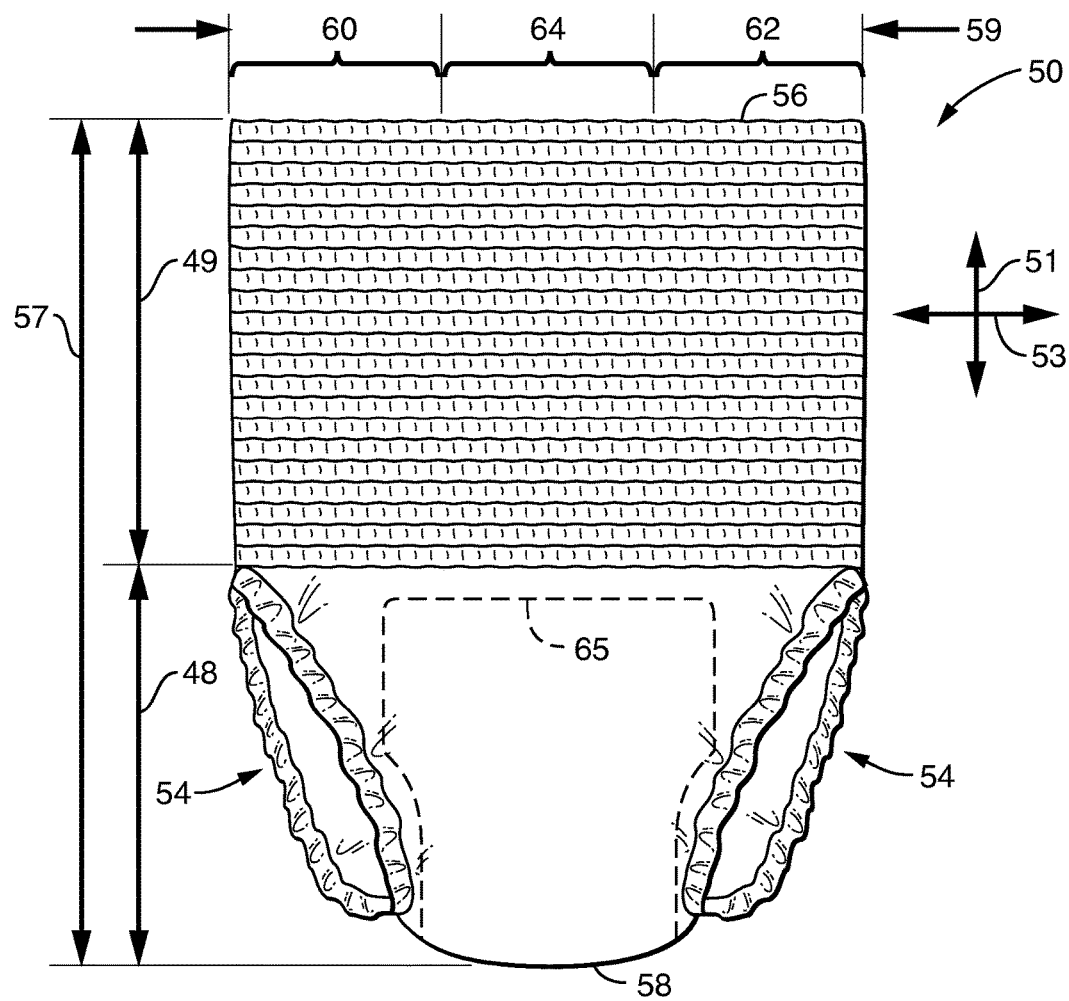
FIG. 6A representatively illustrates a front plan view of an alternative embodiment of a disposable absorbent pant suitable for use in conjunction with certain embodiments of the present invention shown in a relaxed and laid-flat condition.
Figure 6B:
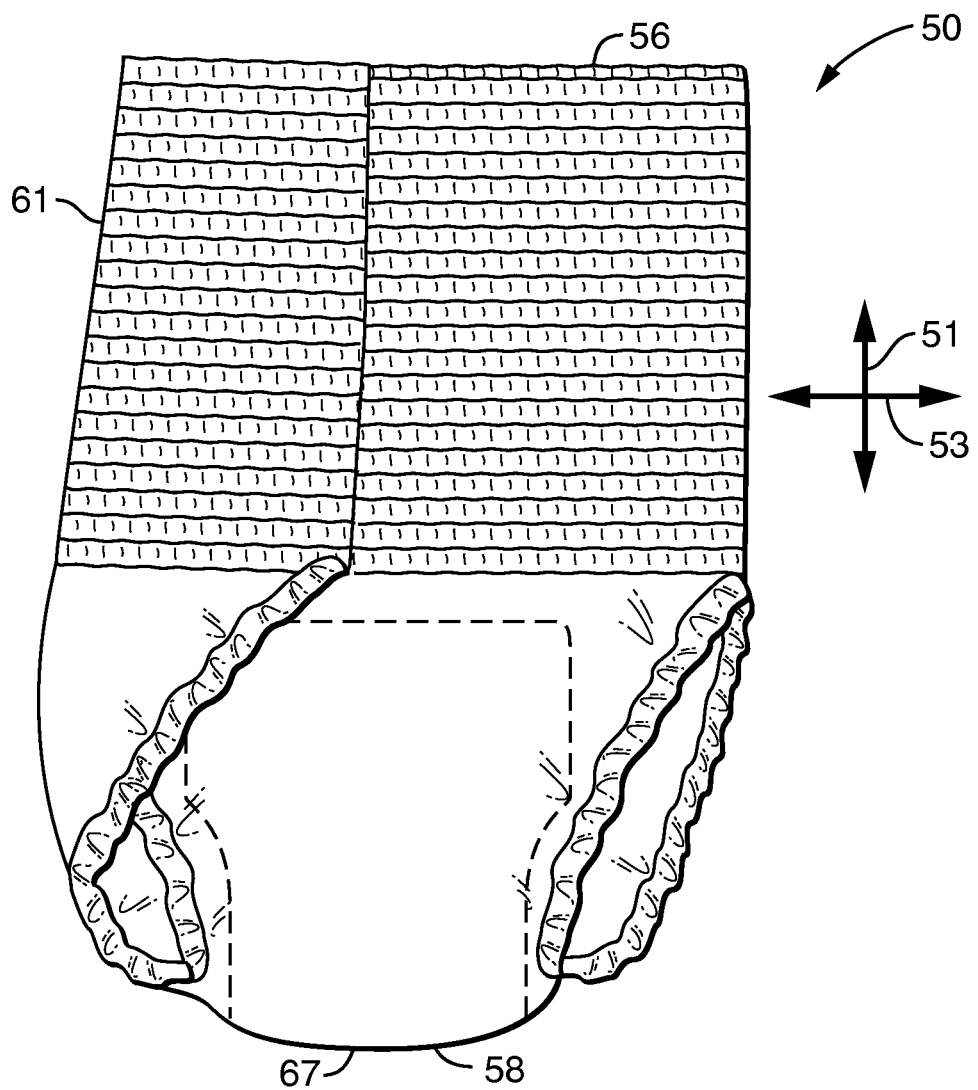
FIG. 6B representatively illustrates a front plan view of the disposable absorbent pant of FIG. 6A, shown in a relaxed and laid-flat condition, with one waist side region folded over the waist center region.
Figure 6C:
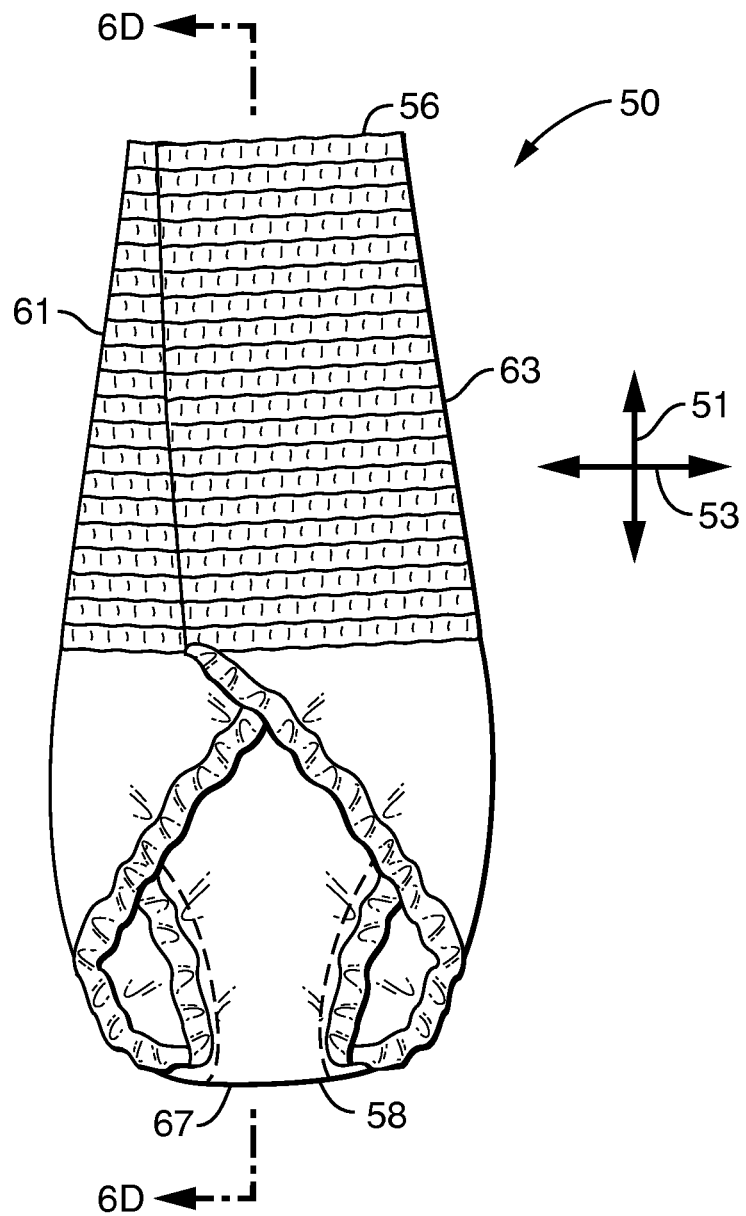
FIG. 6C representatively illustrates a front plan view of the disposable absorbent pant of FIG. 6A, shown in a relaxed and laid-flat condition, with both waist side regions folded over the waist center region.

In particular embodiments, each garment or pant 50 defines a waist opening 52, two leg openings 54, a waist end 56, a crotch end 58, and first and second side edges 55a, 55b. In particular embodiments, each pant includes a pair of side seams 91, 91 which join the front portion of the pant to the back portion. Each pant can include a crotch fold 67. Each pant defines a longitudinal direction 51 that extends from the waist end 56 to the crotch end 58, and each pant defines a transverse direction 53 that is perpendicular to the longitudinal direction 51. Each pant 50 defines an assembled length 57 which extends in the longitudinal direction 51 from the waist end 56 to the crotch end 58. (If the front waistband portion 72 and the back waistband portion 74 are different distances from the crotch end 58, then the assembled length 57 of the pant is the longer of the two distances.) Each pant also defines a width 59 which extends in the transverse direction 53 from one side edge 55a to the other side edge 55b. (If the distance between the first side edge 55a to the second side edge 55b varies depending on where in the longitudinal direction the measurement is taken, then the width 59 is the average distance between side edge 55a and side edge 55b.) The length 57 and width 59 for purposes herein are measured when the pant is in a fully assembled (side seams intact), but otherwise unfolded, relaxed condition, such as that depicted in FIG. 3. The length 57 is measured at the longitudinal centerline of the pant 50, and the width 59 is measured at the longitudinal midpoint of each side seam 55. Each pant further defines a first waist side region 60, a second waist side region 62, and a waist center region 64 positioned transversely between the first waist side region 60 and the second waist side region 62. In particular embodiments, the first waist side region 60 extends approximately 20% to 40% of the transverse width 59 of the pant 50 in an assembled, laid-flat, relaxed condition. The second waist side region 62 extends approximately 20% to 40% of the transverse width 59 of the pant 50 in an assembled, laid-flat, relaxed condition. The waist center region 64 extends approximately 20% to 60% of the width 59 of the pant 50 in an assembled, laid-flat, relaxed condition. In particular embodiments, the first waist side region 60, the second waist side region 62, and the waist center region 64 each extend approximately one-third of the width 59 of the pant 50 in a laid-flat, relaxed condition, as is generally representatively illustrated in FIG. 3. Each waist region 60, 62, 64 extends in the longitudinal direction 51 generally from the waist end 56 to the top of the leg openings 54, 54, as indicated by the arrows 49 in FIGS. 3A and 6A.

In particular embodiments, each pant includes a front panel 71, a back panel 73, and a crotch panel 75. The panels 71,73,75 may be integral with each other, or may comprise separate components attached to one another. In particular embodiments, the front and back panels 71,73 comprise elastomeric materials, such as elastomeric film laminates, elastomeric stranded laminates, elastomeric net or mesh laminates, or the like. In one example, the front and back panels 71,73 each comprise an elastomeric film sandwiched between two polyolefin-based, cloth-like, nonwoven substrates.

Each pant 50 further defines a waistband region 70 which abuts the waist end 56. The waistband region 70 extends in the transverse direction 53 and at least partially encircles the waist opening 52. Each waistband region 70 comprises a front waistband portion 72 and a back waistband portion 74. Each waistband portion 72,74 extends between the side seams 55. The front waistband portion 72 is adapted to contact the front half of a wearer's waist when donned, and the back waistband portion 74 is adapted to contact to the back half of a wearer's waist when donned. The waistband portions 72,74 can be integral with the front and back panels 71,73, or can be separate components that are attached to the front and back panels 71,73. For example, the front waistband portion 72 can constitute the region of the front panel 71 that is within 25 centimeters, or within 35 centimeters, of the front waist edge 76, and the back waistband portion 74 can constitute the region of the back panel 73 that is within 25 centimeters, or within 35 centimeters, of the back waist edge 77. Alternatively, the front waistband portion 72 can comprise a folded-over portion of the front panel 71, and/or the back waistband portion 74 can comprise a folded-over portion of the back panel 73. In particular embodiments, a transversely extending fold line defines the front waist edge 76, and a transversely extending fold line defines the back waist edge 77. In such embodiments, the longitudinal length of the folded portion defines the boundaries of the respective waistband portion. Desirably, one or more elastic strands are disposed within one or both folded-over portions. Examples of particular embodiments of such folded-over waistband configurations are shown in U.S. Patent Application Publication 2008/0134487 to Hartono, which is incorporated by reference to the extent consistent herewith. Alternatively, the front waistband portion 72 can comprise a separate elastomeric component or assembly affixed to the front panel 71, and/or the back waistband portion 74 can comprise a separate elastomeric component or assembly affixed to the back panel 73, as representatively illustrated in FIG. 1. Each pant also defines a crotch region 68 which abuts the crotch end 58. The crotch region 68 extends in the longitudinal direction 51 generally from the crotch end 58 to the tops of the leg openings 54, 54, as indicated by the arrows 48 in FIGS. 3A and 6A.

Each pant also desirably includes an absorbent composite 80 generally disposed in the waist center region 64 and in the crotch region 68. In particular embodiments, the absorbent composite 80 can include a liquid-impermeable garment-side backsheet 82, a liquid-permeable body-side 84, and a fluid-absorbing core 86 comprised of fluff pulp and/or superabsorbent polymer sandwiched between the backsheet 82 and the topsheet 84. The absorbent core 86 has a front edge 87, a back edge 88 spaced from the front edge in the longitudinal direction, and two side edges 89 which extend longitudinally from the front edge 87 to the back edge 88. The absorbent core 86 may be rectangular, hour-glass, oval, trapezoid, or other suitable shape. Due to the additional bulk introduced by an absorbent core 86, the regions of a pant 50 that include an absorbent core 86 are generally thicker than other regions of such pant. Examples of disposable absorbent pants suitable for use in conjunction with the method of the present invention include those disclosed in U.S. Pat. No. 5,745,922 issued May 5, 1998 to Rajala et al., U.S. Pat. No. 6,240,569 issued Jun. 5, 2001 to Van Gompel et al., U.S. 6,702,798 issued Mar. 9, 2004 to Christoffel et al., and U.S. Pat. No. 7,604,624 issued Oct. 20, 2009 to Veith et al., the contents of each of which is hereby incorporated by reference to the extent consistent herewith. Note that the disposable absorbent pants could be provided in a permanently "closed" (i.e., pull-on style) configuration, a releasably and refastenably "closed" configuration, or an "open" (i.e., nonprefastened) configuration—any of which could be used in conjunction with the various embodiments of the present invention.

In particular embodiments, the method 20 includes folding each pant at least once in the longitudinal direction 51. In particular embodiments, as representatively illustrated in FIGS. 4-5, the pant 50 is folded at a transversely extending fold line 44 so as to bring the crotch region 68 into superposed relation (and optionally contacting relation) with the waist center region 64. The crotch end 58 can be positioned to be flush with the waist end 56, as representatively illustrated in FIGS. 5A-D. Alternatively, the crotch end 58 can be positioned to not be flush with the waist end 56, such that the waist end 56 and the crotch end 58 are different distances from the fold line 44. For example, as depicted in FIGS. 4A-D, the pant 50 may be folded such that distance 65 between the crotch end 58 and the fold line 44 is greater than the distance 66 between the waist end 56 and the fold line 44. The first longitudinal fold line 44 can be, but need not be, longitudinally near the front edge 87 of the absorbent core 86, as is the case in the embodiment of FIG. 4. The pant may be folded at fold line 44 such that the crotch region 68 is brought into superposed relation with the front panel 71, or with the back panel 73. In particular embodiments, such as that representatively illustrated in FIGS. 4 and 5, the pant 50 is folded such that the crotch region 68 at least partially directly contacts the back waistband portion 74. In such an embodiment, the garment-side surface 93c of the crotch region 68 of the pant 50 directly contacts the garment side-surface 93w of the back waistband portion 74 of the waistband region 70.

The method 20 defines a machine direction 22, a cross-machine direction 24 that is perpendicular to the machine direction 22, and a vertical direction 26 that is generally perpendicular (and in particular embodiments exactly perpendicular) to both the machine direction 22 and the cross-machine direction 24. "Machine direction" is understood by those of skill in the art, and means the primary direction of travel of product webs or work pieces in a manufacturing process, or in a segment of a manufacturing process. "Generally perpendicular" as used herein means more than 45 degrees, and preferably approximately 90 degrees. While typically the machine direction 22 and cross-machine direction 24 both extend in a plane that runs parallel to the plane defined by the floor of a manufacturing facility, and, accordingly, typically the vertical direction extends in a direction that is perpendicular to the plane defined by the floor of such facility, it is contemplated that the these relationships could be altered. For example, the vertical direction could conceivably extend in a plane that runs parallel to the plane defined by such floor, and either the machine direction or the cross-machine direction could extend in a direction that is perpendicular to the plane defined by such.

The machine direction and the cross-machine direction together define a transport plane. The method in particular embodiments includes transporting the garment in the machine direction 22, such that the longitudinal and transverse directions 51, 53 of the garment lie substantially within the transport plane.

Referring to FIGS. 8-14, the method 20 further includes providing a chute 100. The chute 100 comprises a first side wall 104 and a second side wall 106. The chute 100 optionally includes a back wall 108. The chute 100 defines a chute width 105 that extends from the first side wall 104 to the second side wall 106. The chute defines a first end 121 having a first opening 122, and a second end 123 having a second opening 124. The chute 100 extends from the first end 121 to the second end 123 at least partially, and preferably primarily, in the vertical direction 26, such that the chute side walls 104, 106 extend in the vertical direction 26.

Figure 15:
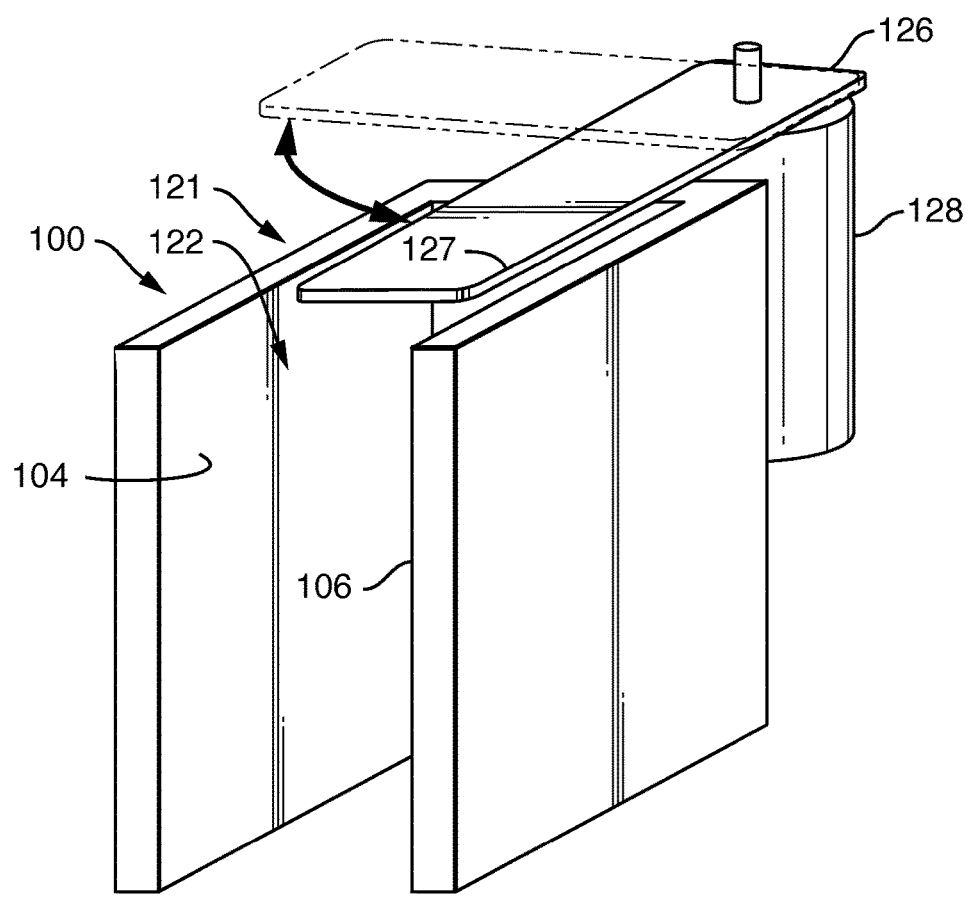
FIG. 15 representatively illustrates a perspective view of one embodiment of a portion of an apparatus suitable for use in conjunction with particular embodiments of the method of the present invention.

The method further includes positioning the garment 50 over the first opening 122 of the chute 100. In particular embodiments, positioning the garment 50 near the first opening 122 of the chute 100 includes supporting the garment at the first opening 122 of the chute 100 using a support device 126. Such optional supporting occurs immediately before the garment 50 is urged into the chute 100, explained below. This brief, temporary step of supporting the garment prior to it being urged into the chute can be accomplished by a timed stream or blast of compressed air, by an oscillating plate or paddle 127 that oscillates over the first opening 122, driven, for example, by an oscillating servo motor 128 (representatively illustrated in FIG. 15), or other suitable means.

The method further includes urging the garment 50 into the chute 100. Preferably, the garment 50 is urged into the chute either by pushing the garment 50 in the vertical direction 26 into the chute 100, or by pulling the garment 50 into the chute 100. For example, in particular embodiments, the garment 50 can be urged into the chute 100 by pushing the garment 50 into the chute 100 using a paddle or paddles 130. Desirably, the paddle defines a paddle width 135, and the paddle width is nearly as wide (e.g., at least 90% as wide) as the chute width 105. In particular embodiments, the garment 50 is attracted to the paddle 130 by vacuum force. For example, the paddle may include a plurality of orifices, and a vacuum may be created in a hollow interior of the paddle, thereby drawing air into the paddle through the orifices, thereby attracting the garment 50 to an outer surface of the paddle 130. In another embodiment, the garment is urged into the chute via the use of timed streams or blasts of compressed air. Preferably, the waist center region 64 and the crotch region 68 of the garment 50 are urged into the chute 100 before the waist side regions 60, 62 are urged into the chute. In particular embodiments, a series of paddles 130 extend from a chain-link or cam mechanism 136, each paddle pushing one of a series of advancing garments 50 into the chute 100, as is representatively illustrated in FIGS. 10 and 13.

In particular embodiments of the method, the chute width 105 extends in a direction that is parallel to the cross-machine direction 24, and the longitudinal direction 51 of each garment 50 is in parallel alignment with the machine direction 22 during the machine-direction transport. Examples of such embodiments are representatively illustrated in FIGS. 11-13. In one desirable variant of such an approach, the garment 50 is transported in the machine direction 22 using a first side conveyor 131, a second side conveyor 132, and a center conveyor 133 positioned between the first side conveyor 131 and the second side conveyor 132. Each conveyor 131/132/133 extends in the machine direction 22. As the garment is transported in the transport plane, the first side conveyor 131 supports the first waist side region 60, the second side conveyor supports the second waist side region 62, and the center conveyor supports the waist center region 64 and the crotch region 68. In particular embodiments, the center conveyor 133 defines a center conveyor end 134. The chute 100 is positioned at or adjacent the center conveyor end 134. Desirably, the first side conveyor 131 extends in the machine direction 22 past the center conveyor end 134 and extends adjacent the first side wall 104 of the chute 100. Likewise, and the second side conveyor 132 desirably extends in the machine direction 22 past the center conveyor end 134 and extends adjacent the second side wall 106 of the chute. Positioning the garment 50 over the first opening 122 of the chute 100 includes supporting the garment 50 with the first and second side conveyors 131, 132. In such an embodiment, when the garment 50 is positioned over the first opening 122, the garment 50 is preferably substantially not supported by the center conveyor 133.

In other embodiments of the method, the chute width 105 extends in a direction that is parallel to the machine direction 22, and the longitudinal direction 51 of each garment 50 is in parallel alignment with the cross-machine direction 24 during the machine-direction transport. Examples of such embodiments are representatively illustrated in FIGS. 8-10 and 14. In one variant of such an approach, each garment 50 is separated from an interconnected series 150 of garments prior to being positioned over the first opening 122 of the chute 100. In another variant, each garment 50 is separated from an interconnected series of garments simultaneously with urging the garment into the chute. For example, lines of weakness (such as a line of perforations) can be created in the interconnected series of garments. When each garment 50 is urged into the chute 100, the garment 50 is simultaneously separated from the interconnected series of garments along the line of weakness. In particular embodiments, such as the embodiments of FIG. 8-14, each garment 50 is folded along the respective transversely extending fold line 44 prior to arrival at chute 100.

In particular embodiments, such as those representatively illustrated in FIGS. 8-10 and 14, the first side wall 104 comprises a first side conveyor, and the second side wall 106 comprises a second side conveyer. In such an embodiment, the first and second side conveyors can act to transport the garment in the vertical direction 26. In particular embodiments in which the side walls comprise side conveyors, the back wall 108 can optionally comprise a back conveyer, and the first side conveyor, the second side conveyor, and the back conveyor advance together in the vertical direction 22. In other embodiments, such as those representatively illustrated in FIGS. 11-13, both the first and second side walls 104, 106 are stationary. In certain embodiments, both the first and second side walls 104, 106 (whether stationary or non-stationary) comprise vacuum holes through which vacuum forces are imparted, and the vacuum forces attract the garment 50 to the first and second side walls 104, 106 at desired regions.

Figure 16:
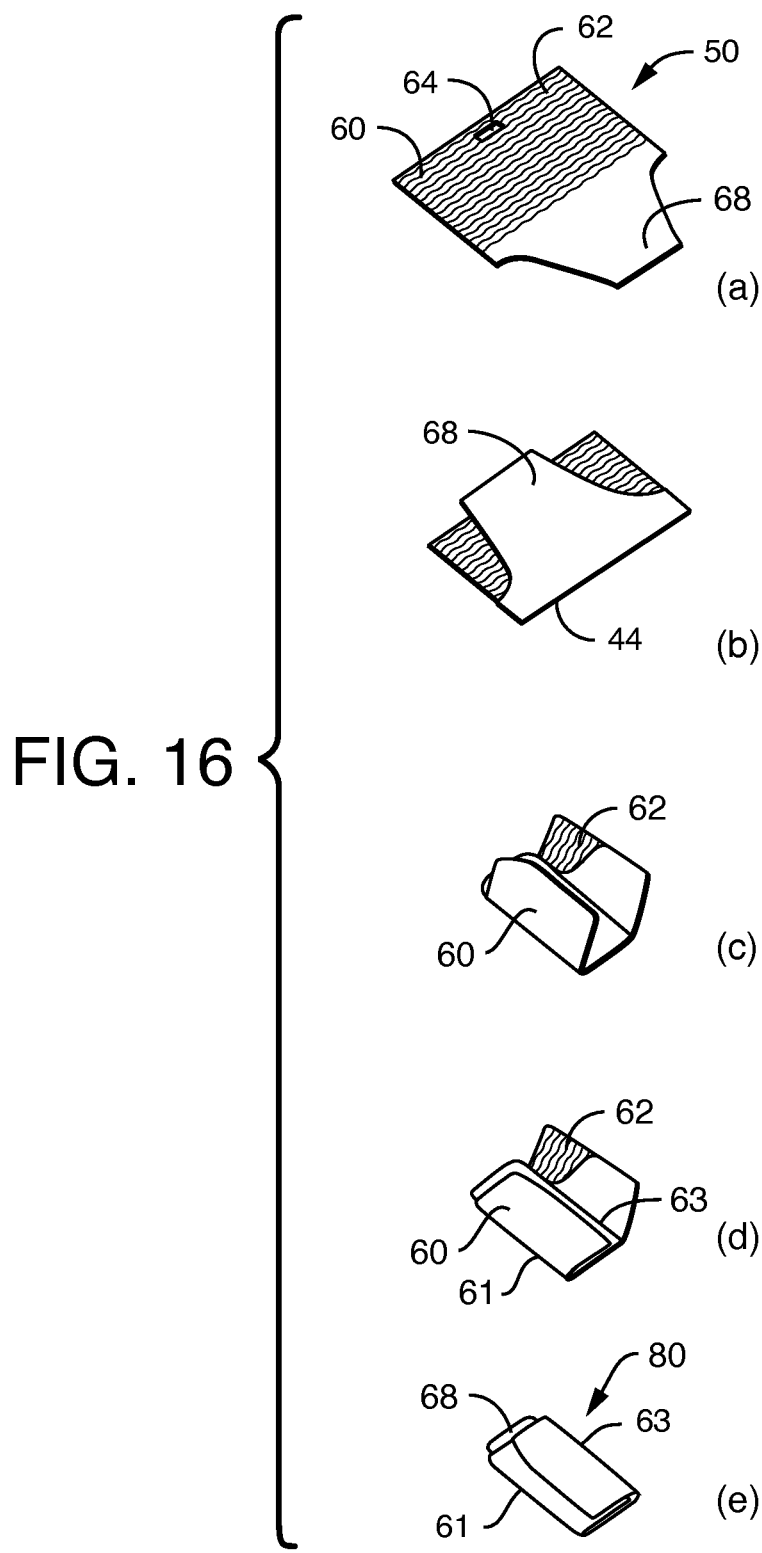
FIG. 16 representatively illustrates a perspective view of various stages of folding a garment in general accordance with the exemplary embodiments of FIGS. 8-14.
Figure 17:
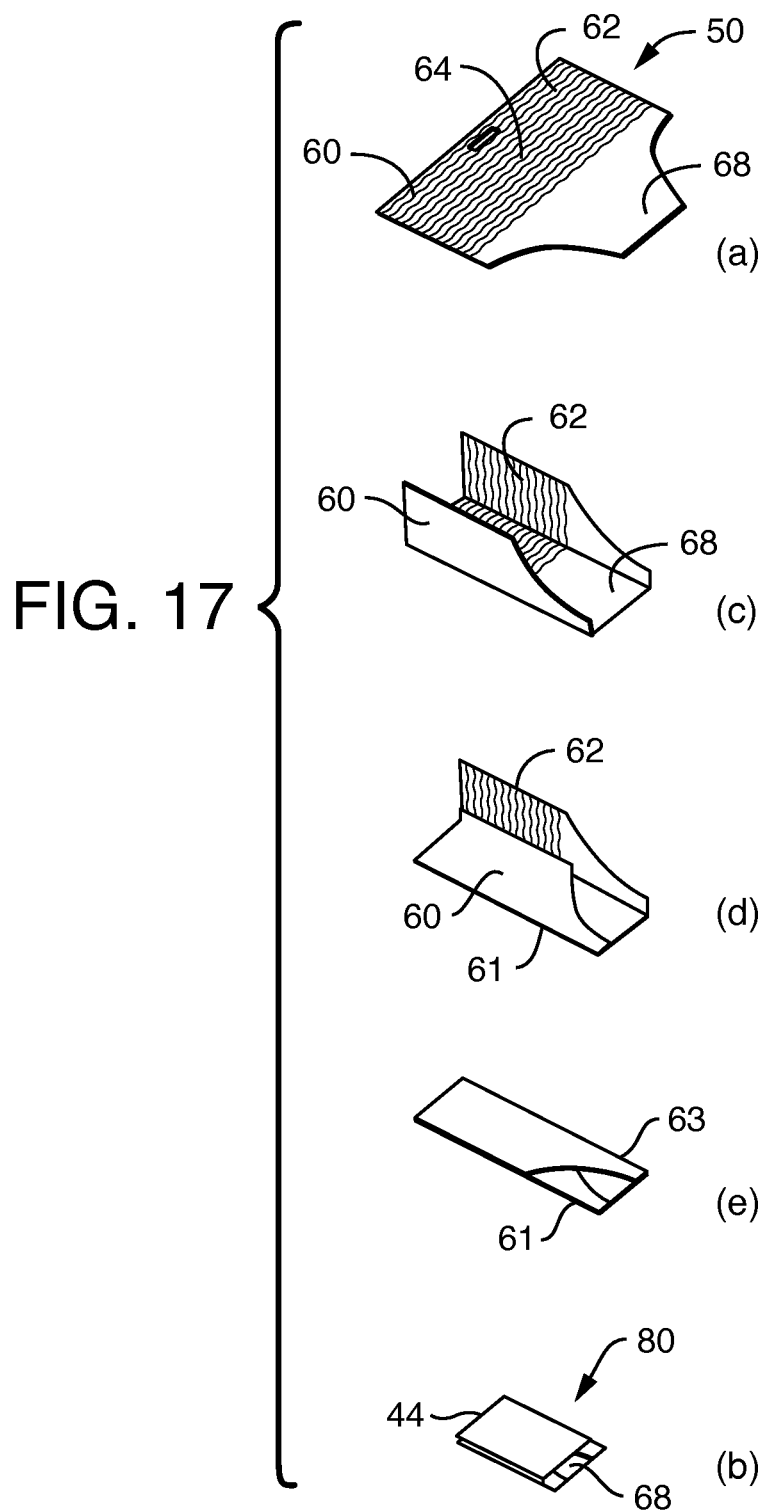
FIG. 17 representatively illustrates a perspective view of various stages of folding a garment similar to the stages shown in FIG. 16, but with a change made to the order of the folding steps.

After the garment 50 has been urged into the chute 100, the method further includes folding the garment 50 at least once, and preferably twice, in the transverse direction 53 of the garment 50. FIGS. 8-14 show garments 50 in various stages of folding while in a chute 100. FIGS. 16-17 depict various stages of folding that can be accomplished using a chute in particular embodiments of the present invention, but with the chute and associated apparatus removed to more clearly depict the various folding stages. In particular embodiments, as representatively illustrated in FIGS. 8-14 and 16-17, the first waist side region 60 and the second waist side region 62 of each pant 50 are folded over, or moved into superposed relation with, the waist center region 64. For example, the method can include folding the garment 50 along a longitudinally extending first fold line 61 so as to position the first waist side region 60 over the waist center region 64. Preferably, the first fold line 61 is adjacent the first side wall 104. Similarly, the method can include folding the garment 50 along a longitudinally extending second fold line 63 so as to position the second waist side region 62 over the waist center region 64. Preferably, the second fold line 63 is adjacent the second side wall 106. In particular embodiments, the first waist side region 60 is folded over the waist center region 64, and the second waist side region 62 is folded over both the waist center region 64 as well as the first waist side region 60. In this way, the pant 50 is in particular embodiments folded twice in the transverse direction 53.

Figure 7A:
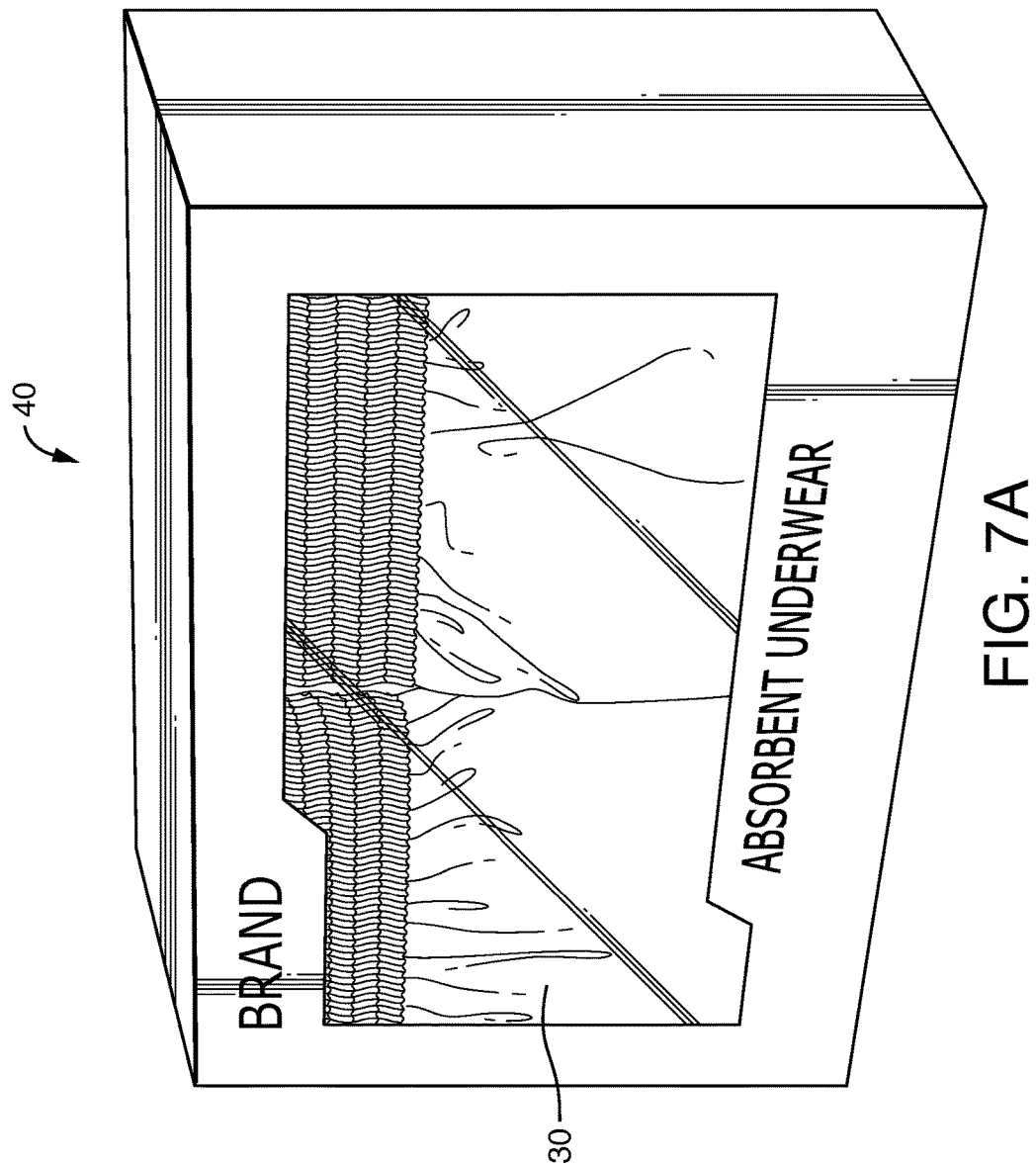
FIG. 7A representatively illustrates a perspective view of one embodiment of a package of disposable absorbent garments folded using particular embodiments of the present invention.
Figure 7B:
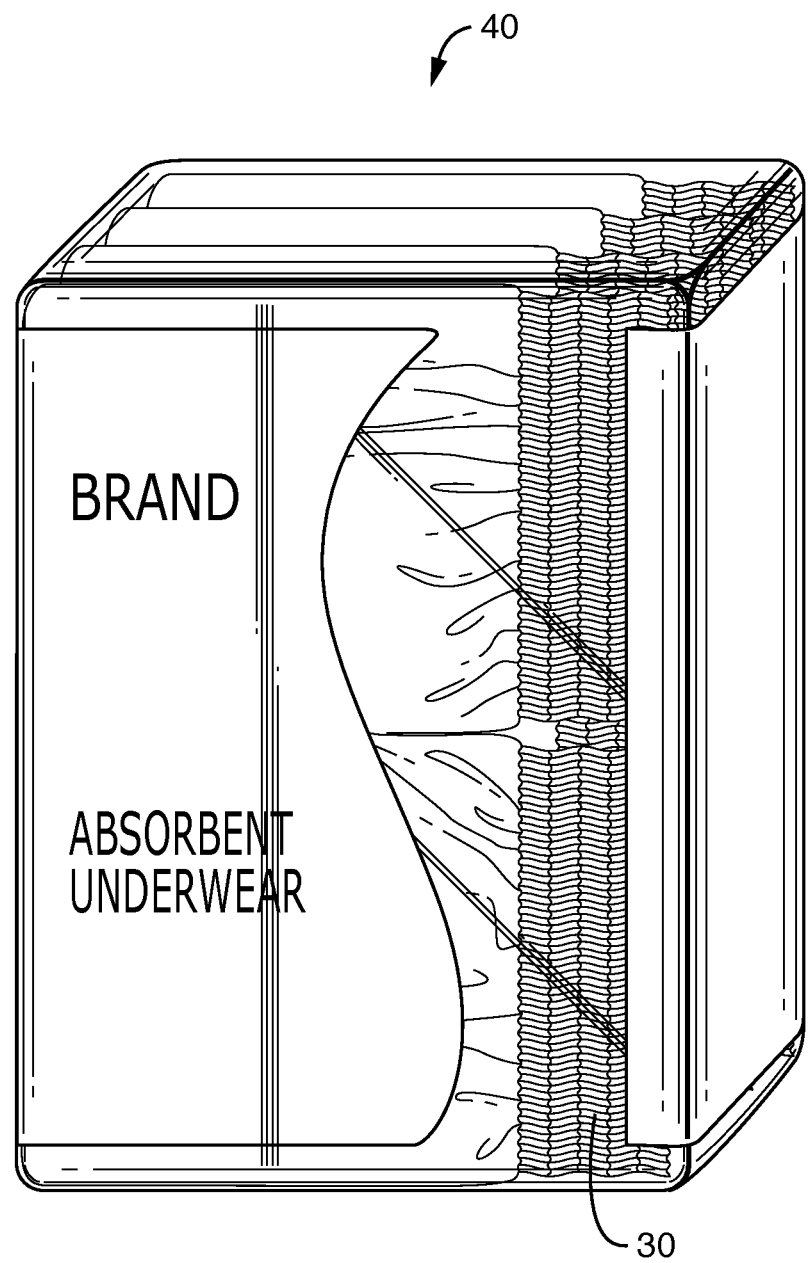
FIG. 7B representatively illustrates a perspective view of an alternative embodiment of a package of disposable absorbent garments folded using particular embodiments of the present invention.

As set forth earlier, the method preferably includes folding each pant at least once in the longitudinal direction 51, such as at a transversely extending fold line 44, to bring the crotch region 68 into superposed relation with the waist center region 64. In particular embodiments, folding of the garment along the transversely extending fold line 44 occurs before folding of the garment along the first and second fold lines 61, 63. Examples of this approach are representatively illustrated in FIGS. 8-14 and 16. Stated another way, in particular embodiments, the pant 50 is folded at least once in the longitudinal direction 51 so as to position the crotch end 58 in close proximity to the waist end 56 before the pant 50 is folded in the transverse direction 53. For example, as representatively illustrated in the embodiment of FIGS. 4 and 5, the pant 50 is first folded at a transversely extending fold line 44, is thereafter folded at a longitudinally extending first fold line 61, and is finally folded at a longitudinally extending second fold line 63. In the folded configuration depicted in FIG. 5, the majority of the crotch region 68 is at least partially sandwiched between the first waist side region 60 and the center waist region 64. In particular embodiments, such as that representatively illustrated in FIG. 5, both the front waistband portion 72 and the back waistband portion 74 of the waistband region 70 are wrapped around the crotch region 68. In such embodiments, it can be desirable to have the waistband region 70 of the pant in a tensioned condition. Having the waistband region 70 in a tensioned or partially taut condition can assist in highlighting the "real underwear"-like properties of the pant to a consumer viewing the pant, such as through a transparent window region 30 of a package 40, as shown in FIGS. 7A and 7B.

In other embodiments, folding of the garment along the transversely extending fold line 44 occurs after folding of the garment along the first and second fold lines 61, 63. Examples of this approach are representatively illustrated in FIGS. 6A-E and FIG. 17. The first waist side region 60 and the second waist side region 62 of each pant 50 are first folded over, or moved into superposed relation with, the waist center region 64. Thereafter, the garment is folded at the transversely extending fold line 44 so as to bring the crotch region 68 into superposed relation with the waist center region 64.

Referring to FIGS. 1, and 3B, in particular embodiments, the absorbent core 86 defines a maximum core width 85. "Maximum core width" as used herein means the longest transverse distance between the first and second core side edges 89, 89. The maximum core width 85 is determined by examining the garment in a fully assembled (side seams intact), but otherwise unfolded, relaxed condition, such as that depicted in FIG. 3. In particular embodiments, such as that representatively illustrated in FIG. 3B, the maximum core width 85 exceeds the chute width 105, such that the first fold line 61 and the second fold line 62 each extend into the absorbent core 86. In particular embodiments, the method of the present invention can deliver consistent, robust folds of the waist side regions 60, 62, despite the presence of relatively thick and bulky absorbent core "ears" in the territory of the fold lines 61, 63.

Figure 8:
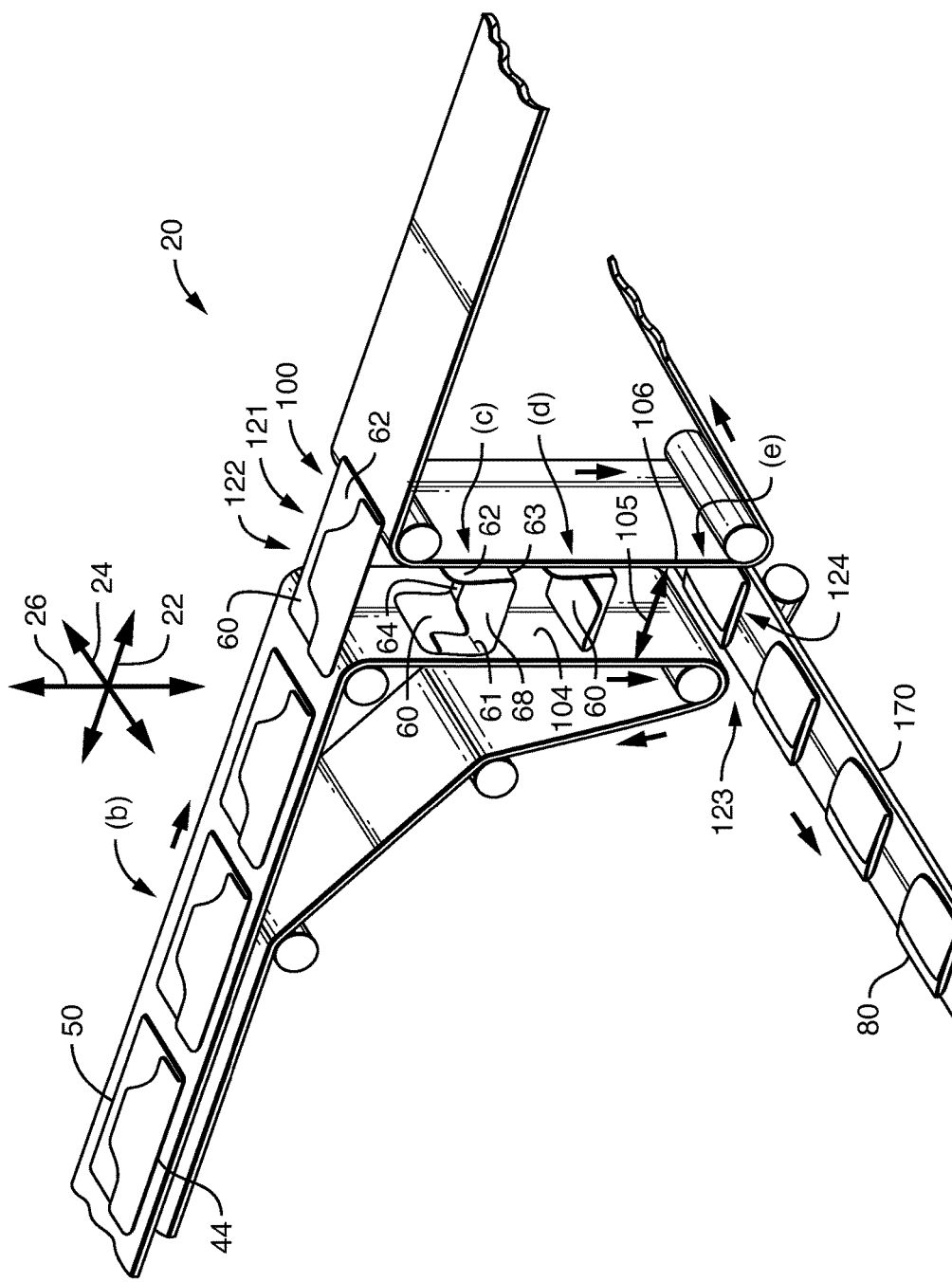
FIG. 8 representatively illustrates a perspective view of one embodiment of the method of the present invention.

FIGS. 8 and 16-17 representatively illustrate stages of garment folding while in a chute (chute not shown in FIGS. 16 and 17). In step (a), the pant-like garment 50 exists in an unfolded, laid-flat condition, such as a relaxed, unfolded, laid-flat condition. In step (b), the garment 50 has been folded at the transversely extending fold line 44 so as to bring the crotch region 68 into superposed and contacting relation with the waist center region 64. In step (c), the waist center region 64 and the crotch region 68 of the garment 50 are urged into the chute 100. In step (d), the garment 50 is folded along a longitudinally extending first fold line 61 so as to position the first waist side region 60 over the waist center region 64. The first fold line 61 is adjacent the first side wall 104. In step (e), the garment 50 is folded along a longitudinally extending second fold line 63 so as to position the second waist side region 62 over the waist center region 64. The second fold line 63 is adjacent the second side wall 106. After the garment 50 is thus folded twice in the transverse direction 53, the garment in particular embodiments exits the chute 100. In particular embodiments, the fully folded garment 80 exits the chute directly onto an exit conveyor. Note that step (b) can either occur before steps (c)-(e) (e.g., FIGS. 8-14 and 16) or after steps (c)-(e) (e.g., FIG. 17).

The transverse folding of the first and second waist side regions 60, 62 in the chute 100 can be accomplished by any of a variety of techniques. For example, folding the garment along the first and second fold lines 61, 63 can be accomplished via the use of protruding folding blades. For example, as the garment 50 travels in the vertical direction 26 within the chute 100, a pair of folding blades can protrude into each trough through slots present in respective side walls 104, 106. The motion of the blades is configured to make contact with the waist side regions 60, 62, and to fold the waist side regions 60, 62 over the waist center region 64. In an alternative example, folding the garment along the first and second fold lines is accomplished via a pair of compressed streams or blasts of air, such as compressed blasts of air blown into the chute 100 from orifices present in the side walls 104, 106.

Figure 9:
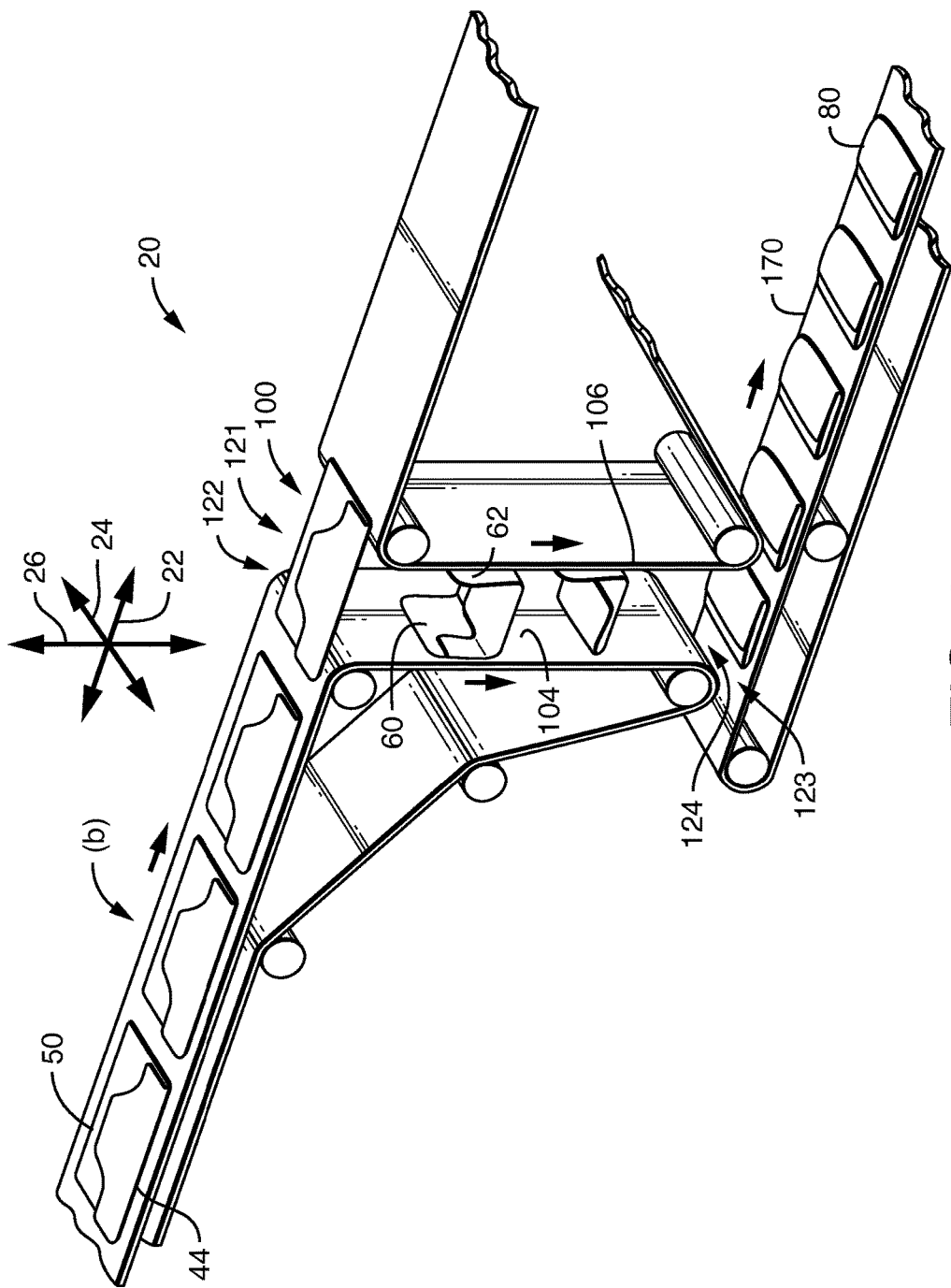
FIG. 9 representatively illustrates a perspective view of another embodiment of the method of the present invention.
Figure 12:
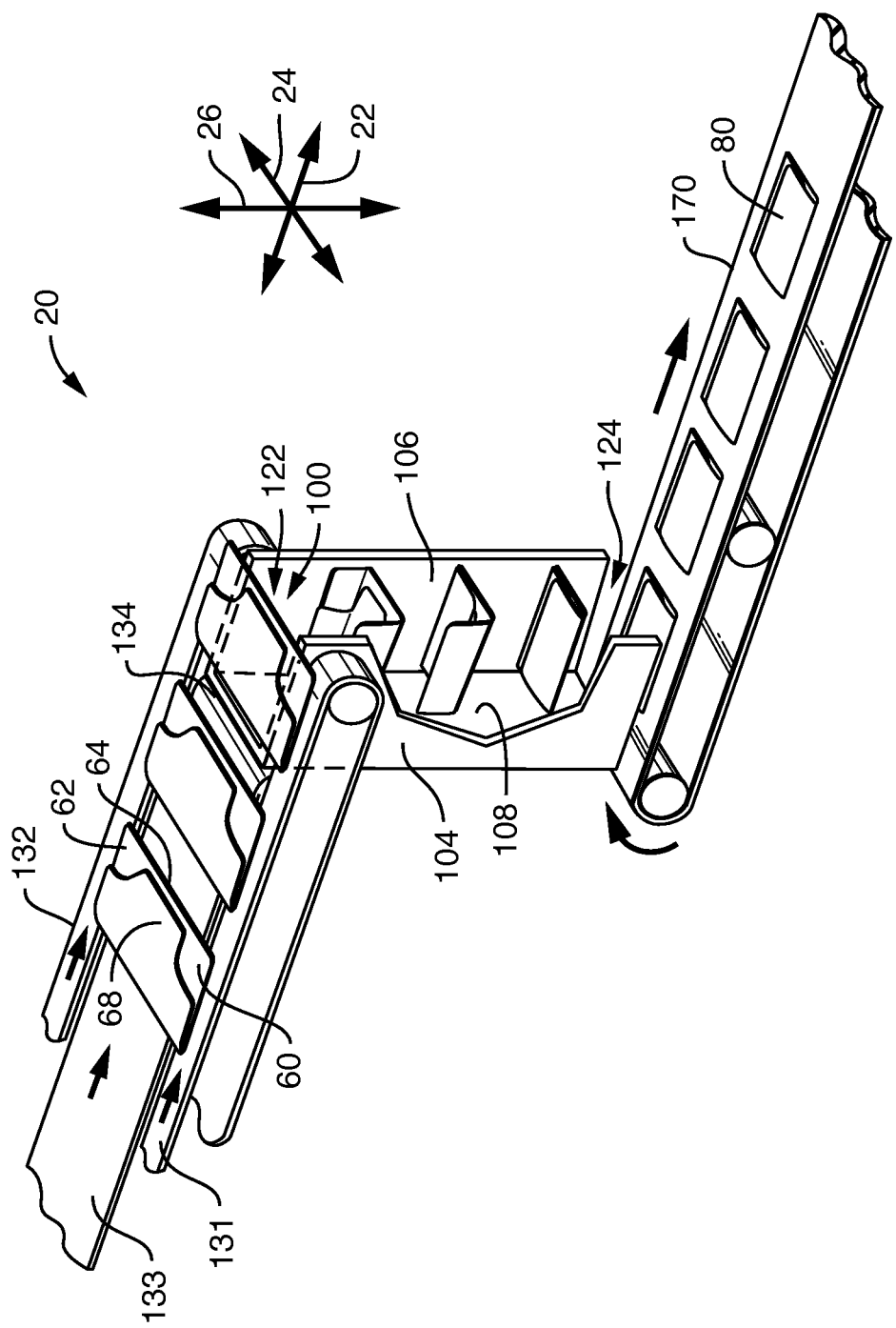
FIG. 12 representatively illustrates a perspective view of yet another embodiment of the method of the present invention, with portions cut away to show underlying features.
Figure 13:
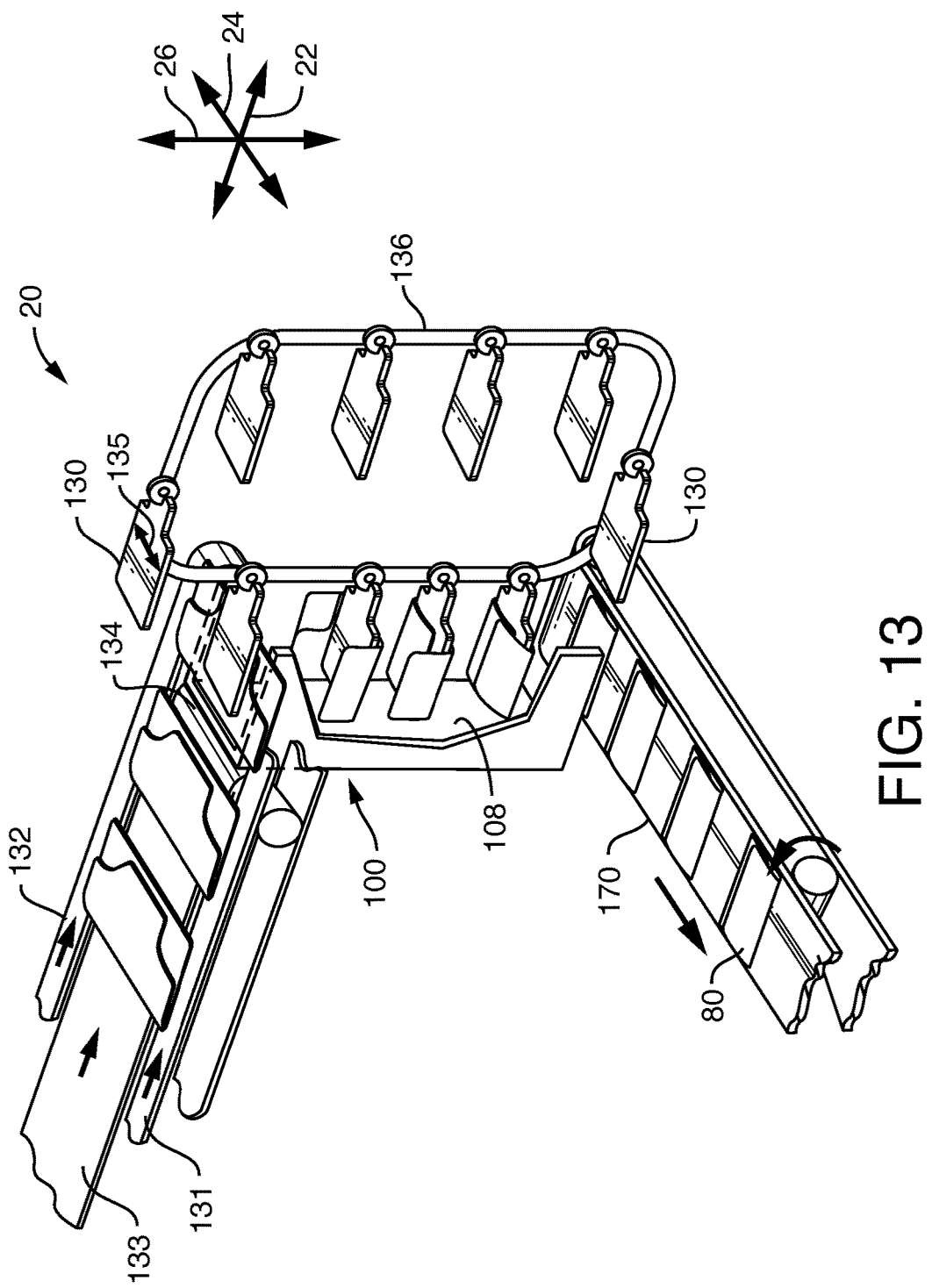
FIG. 13 representatively illustrates a perspective view of still another embodiment of the method of the present invention, with portions cut away to show underlying features.

The fully folded garment 80 exits the chute 100 through the second opening 124. In particular embodiments, the fully folded garment 80 exits the chute onto an exit conveyor 170, such as a vacuum conveyor. In particular embodiments, the exit conveyor 170 extends in and transports the garment 80 in the machine direction 22. Examples of such embodiments are shown in FIGS. 9 and 12. In other embodiments, the exit conveyor 170 extends in and transports the garment 80 in the cross-machine direction. Examples of such embodiments are shown in FIGS. 8, 10, 11, 13, and 14.

Figure 10A:
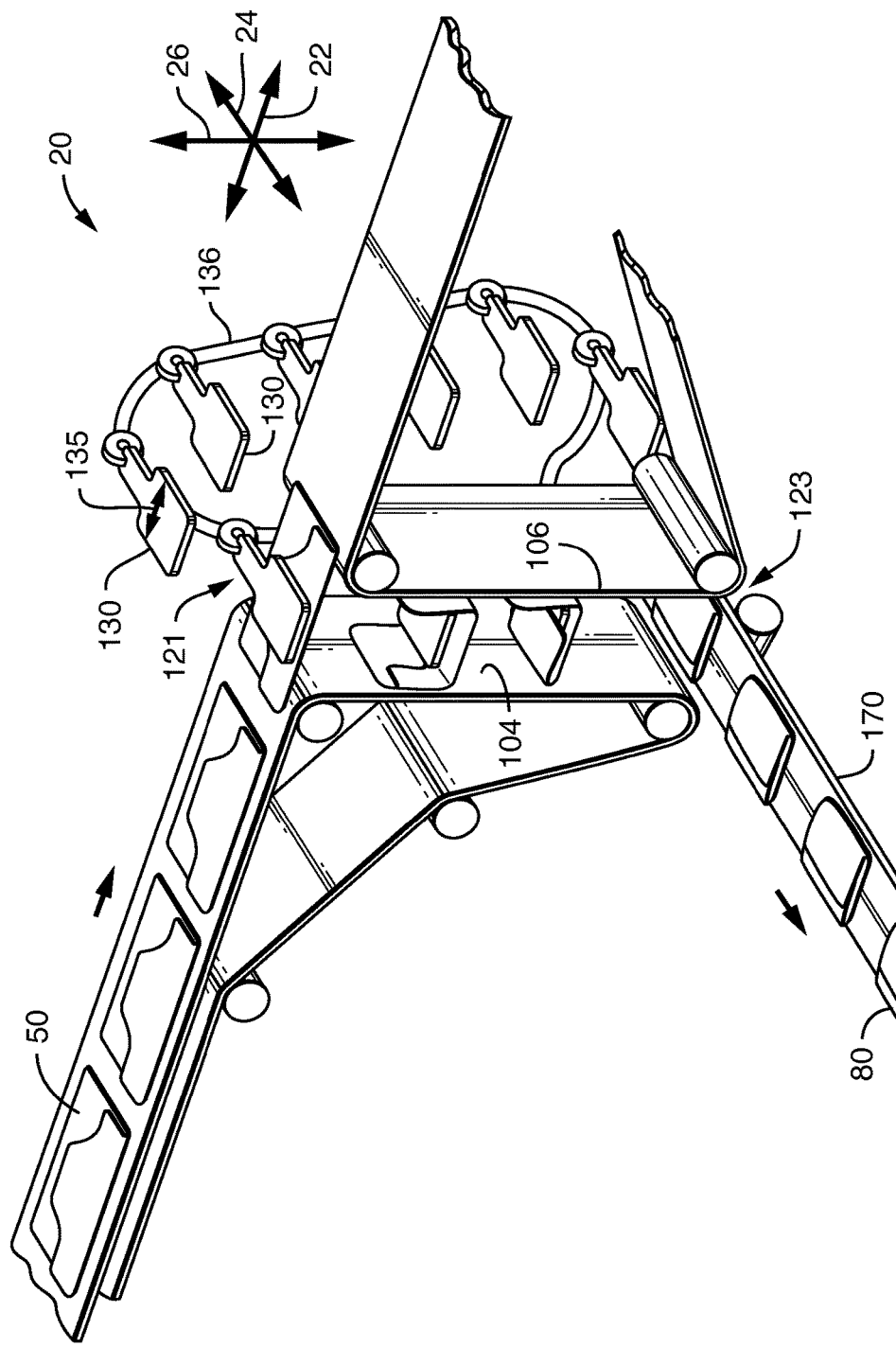
FIG. 10A representatively illustrates a perspective view of yet another embodiment of the method of the present invention.
Figure 10B:
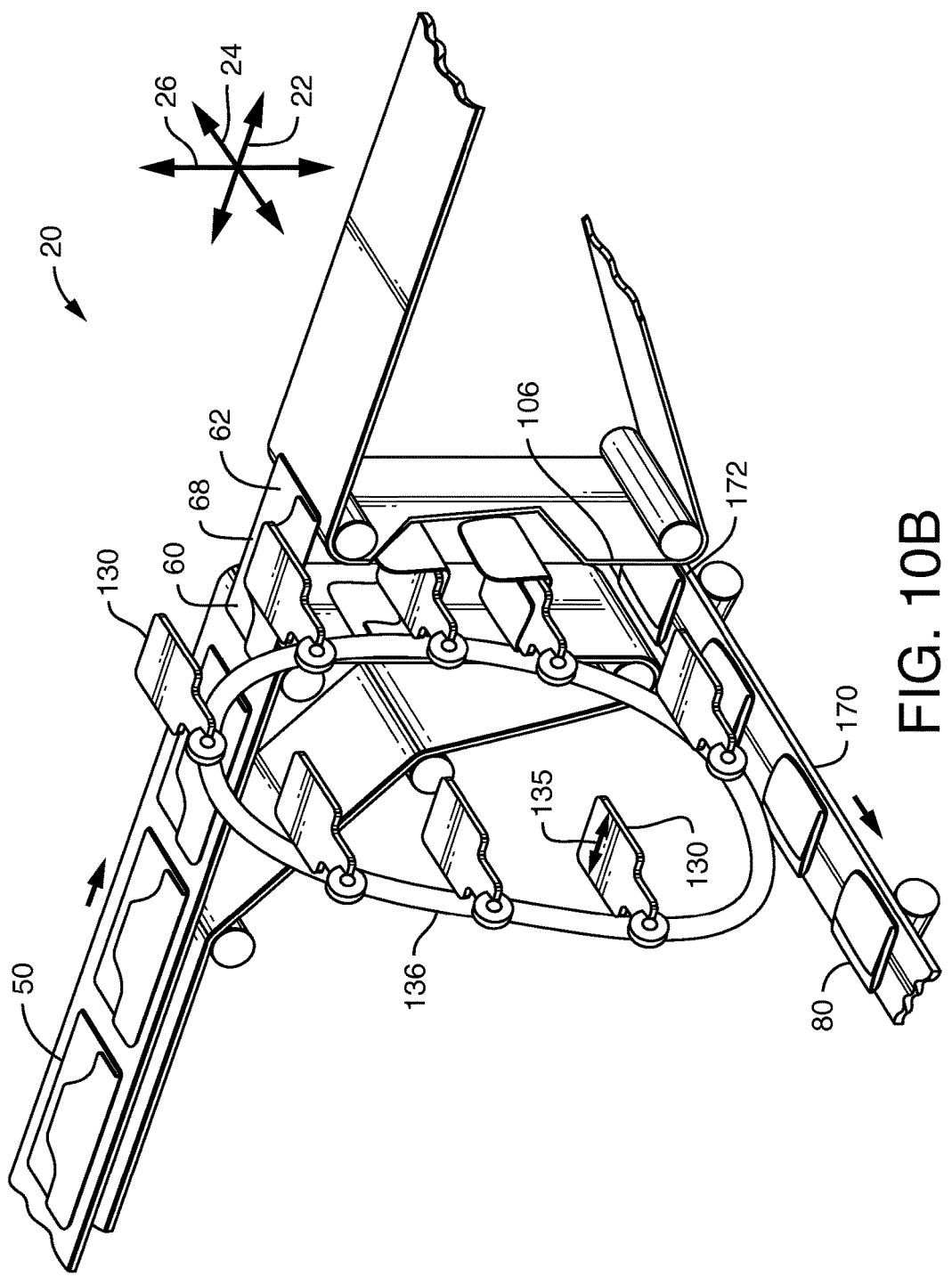
FIG. 10B representatively illustrates a perspective view of an embodiment similar to the embodiment shown in FIG. 10A, but with certain components in different positions, and with portions cut away to show underlying features.
Figure 11:
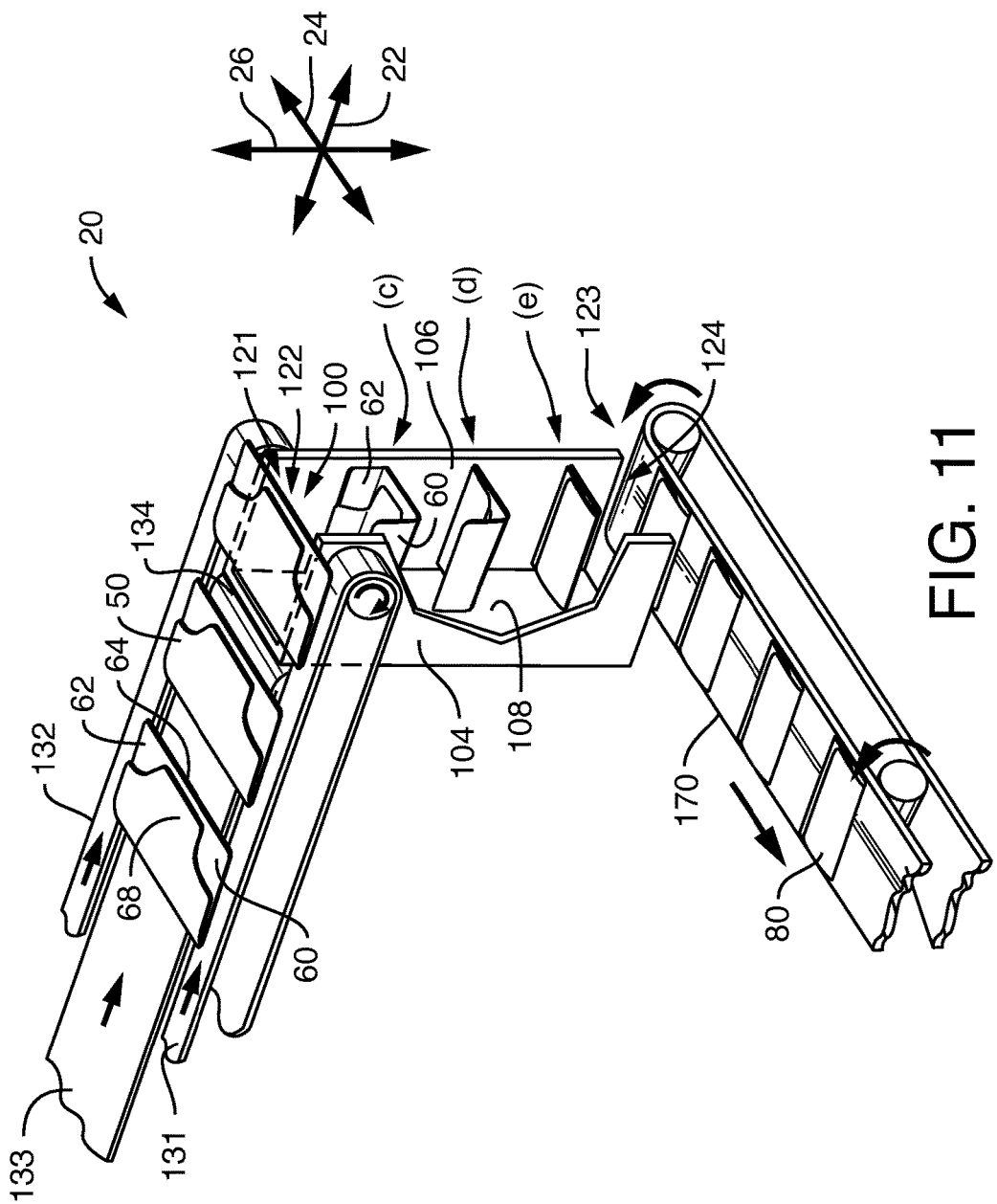
FIG. 11 representatively illustrates a perspective view of still another embodiment of the method of the present invention, with portions cut away to show underlying features.

In embodiments in which a paddle 130 is used to move the garment through the chute to the exit conveyor 170, the paddle, at the point of delivery 172 of the garment 80 to the exit conveyor 170, can travel in substantially the same direction as the exit conveyor 170. An example of such embodiments is shown in FIG. 10B. In certain versions of such embodiments, the paddle 130, at the point of delivery 172 of the garment 80 to the exit conveyor 170, is traveling at a greater rate of speed than the exit conveyor 170. In this way, the paddle 130 can withdraw from the folded garment 80 as the garment 80 is deposited onto the slower moving exit conveyor 170.

Figure 14:
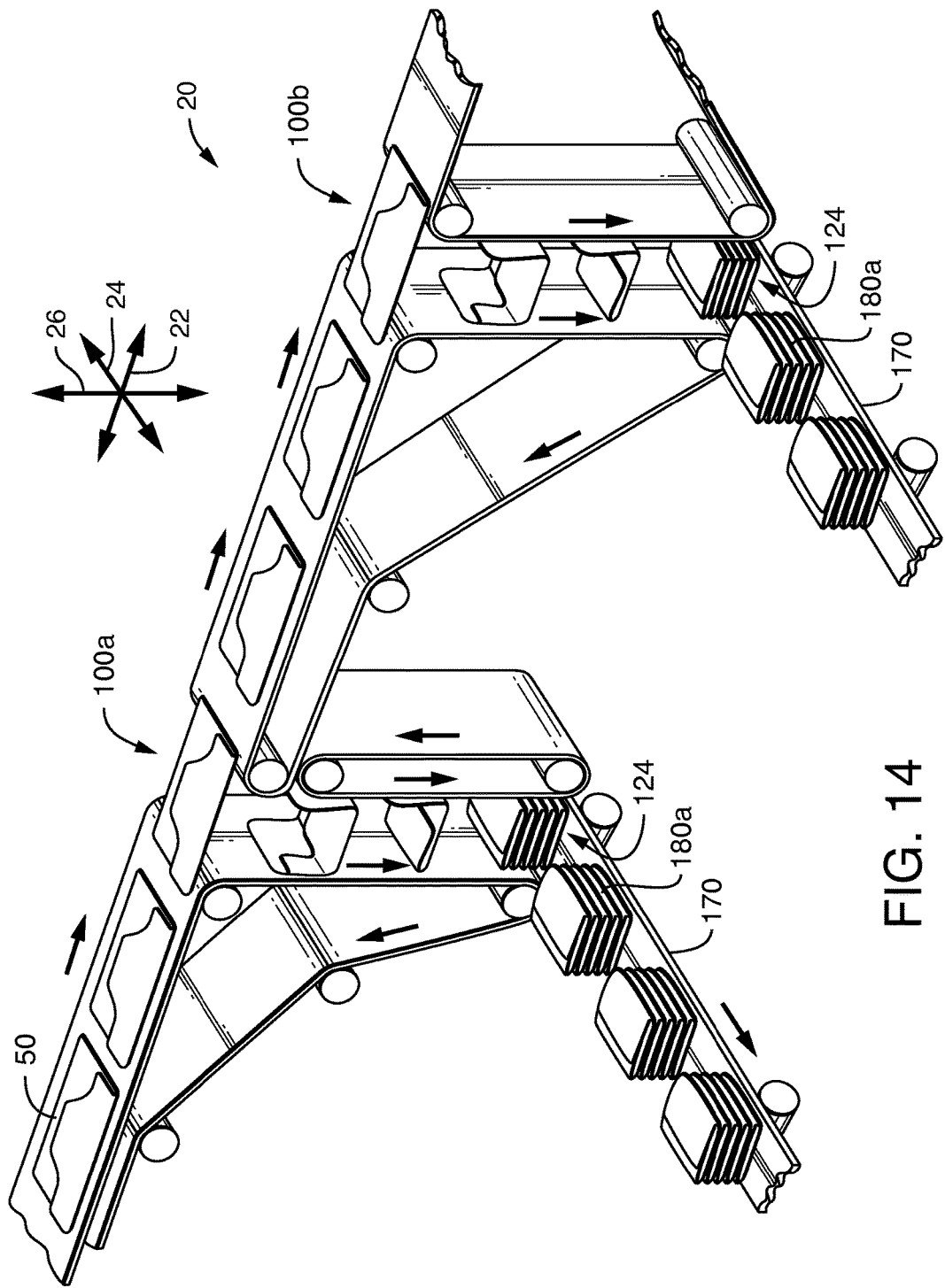
FIG. 14 representatively illustrates a perspective view of yet another embodiment of the method of the present invention.

Referring to FIG. 14, in particular embodiments of the method, a stack 180 of fully folded garments 80 is formed or accumulated at the second opening 124 of the chute 100. Eventually, the stack 180 is pushed out of the chute 100 through the second opening 124. Optionally, the stack 180 can be pushed onto an exit conveyor 170, as representatively illustrated in FIG. 14. Alternatively, the stack 180 can be pushed directly into a stacker (not shown). In one variant, shown in FIG. 14, the method 20 includes first and second chutes 100a, 100b. When a stack 180a is being pushed out of the first chute 100a, the garments 50 are transported to and urged into the second chute 100b for folding and accumulating. Conversely, when a stack 180b is being pushed out of the second chute 100b, the garments 50 are transported to and urged into the first chute 100a for folding and accumulating.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of folding a pant-like disposable absorbent garment, the method defining a machine direction, a cross-machine direction, and a vertical direction generally perpendicular to both the machine direction and the cross-machine direction, the machine direction and the cross-machine direction together defining a transport plane, the method comprising:

providing said garment, said garment having a waist opening and two leg openings, said garment defining a longitudinal direction and a transverse direction, said garment defining a first waist side region adjacent a first side edge, a second waist side region adjacent a second side edge, a waist center region positioned transversely between the first waist side region and the second waist side region, and a crotch region longitudinally adjacent the waist center region, the garment further including an absorbent core;

providing a chute, the chute comprising a first side wall and a second side wall, the chute defining a chute width extending from the first side wall to the second side wall, the chute defining a first end having a first opening and a second end having a second opening, the chute extending from the first end to the second end in the vertical direction;

transporting the garment in the machine direction, such that the longitudinal and transverse directions of the garment lie substantially within the transport plane;

positioning the garment over the first opening of the chute;

urging the garment into the chute;

transporting the garment in the vertical direction within the chute; and folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the garment is in the chute.

2. The method of claim 1, wherein the absorbent core defines a longitudinally extending first core side edge and a longitudinally extending second core side edge, the core defining a maximum core width, wherein the maximum core width exceeds the chute width, such that the first fold line and the second fold line each extend into the absorbent core.

3. A method of folding a pant-like disposable absorbent garment, the method defining a machine direction, a cross-machine direction, and a vertical direction generally perpendicular to both the machine direction and the cross-machine direction, the machine direction and the cross-machine direction together defining a transport plane, the method comprising:
provided said garment, said garment having a waist opening and two leg openings, said garment defining a longitudinal direction and a transverse direction, said garment defining a first waist side region adjacent a first side edge, a second waist side region adjacent a second side edge, a waist center region positioned transversely between the first waist side region and the second waist side region, and a crotch region longitudinally adjacent the waist center region, the garment further including an absorbent core;
providing a chute, the chute comprising a first side wall and a second side wall, the chute defining a chute width extending from the first side wall to the second side wall, the chute defining a first end having a first opening and a second end having a second opening, the chute extending from the first end to the second end in the vertical direction;
transporting the garment in the machine direction, such that the longitudinal and transverse directions of the garment lie substantially within the transport plane;
positioning the garment over the first opening of the chute;
urging the garment into the chute;
transporting the garment in the vertical direction within the chute;
folding the garment along a longitudinally extending first fold so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the garment is in the chute; and
folding the garment along a transversely extending fold line so as to bring the crotch region into superposed relation with the waist center region, wherein said folding the garment along the transversely extending fold line occurs before folding the garment along the first and second fold lines.

4. A method of folding a pant-like disposable absorbent garment, the method defining a machine direction, a cross-machine direction, and a vertical direction generally perpendicular to both the machine direction and the cross-machine direction, the machine direction and the cross-machine direction together defining a transport plane, the method comprising:
providing said garment, said garment having a waist opening and two leg openings, said garment defining a longitudinal direction and a transverse direction, said garment defining a first waist side region adjacent a first side edge, a second waist side region adjacent a second side edge, a waist center region positioned transversely between the first waist side region and the second waist side region, and a crotch region longitudinally adjacent the waist center region, the garment further including an absorbent core;
providing a chute, the chute comprising a first side wall and a second side wall, the chute defining a chute width extending from the first side wall to the second side wall, the chute defining a first end having a first opening and a second end having a second opening, the chute extending from the first end to the second end in the vertical direction;
transporting the garment in the machine direction, such that the longitudinal and transverse directions of the garment lie substantially within the transport plane;
positioning the garment over the first opening of the chute;
urging the garment into the chute;
transporting the garment in the vertical direction within the chute; and
folding the garment along a longitudinally extending first fold line, the first fold line being adjacent the first side wall, and folding the garment along a longitudinally extending second fold line, the second fold line being adjacent the second side wall, wherein both such folding steps occur while the garment is in the chute.

* * * * *